US008796431B2

(12) United States Patent
Stowell et al.

(10) Patent No.: US 8,796,431 B2
(45) Date of Patent: Aug. 5, 2014

(54) EFFICIENT PRODUCTION OF PEPTIDES

(75) Inventors: Michael H. B. Stowell, Boulder, CO (US); Jonathan Caruthers, Boulder, CO (US); Travis Nemkov, Boulder, CO (US); Brian Hiester, Boulder, CO (US); Leslie Boux, Boulder, CO (US); Mikhail Plam, Boulder, CO (US)

(73) Assignees: The Regents of the University of Colorado, a body corporate, Denver, CO (US); AmideBio LLC, Boulder, CO (US)

( * ) Notice: Subject to any disclaimer, the term of this patent is extended or adjusted under 35 U.S.C. 154(b) by 0 days.

(21) Appl. No.: 12/942,450

(22) Filed: Nov. 9, 2010

(65) Prior Publication Data

US 2011/0112990 A1    May 12, 2011

Related U.S. Application Data

(60) Provisional application No. 61/259,367, filed on Nov. 9, 2009.

(51) Int. Cl.
| | | |
|---|---|---|
| *C07K 17/02* | (2006.01) | |
| *C12P 21/04* | (2006.01) | |
| *C12P 21/06* | (2006.01) | |
| *C12N 9/90* | (2006.01) | |
| *C07K 14/62* | (2006.01) | |
| *C07K 14/65* | (2006.01) | |
| *C07K 14/61* | (2006.01) | |
| *C07K 14/655* | (2006.01) | |
| *C07K 14/585* | (2006.01) | |
| *C07K 14/47* | (2006.01) | |
| *C07K 14/005* | (2006.01) | |
| *C07K 14/635* | (2006.01) | |
| *C07K 14/56* | (2006.01) | |
| *C12N 15/70* | (2006.01) | |
| *C07K 14/535* | (2006.01) | |
| *C07K 14/505* | (2006.01) | |
| *C07K 14/755* | (2006.01) | |
| *G06Q 99/00* | (2006.01) | |
| *C07K 14/605* | (2006.01) | |

(52) U.S. Cl.
CPC ............ *C07K 14/4711* (2013.01); *C12P 21/06* (2013.01); *C12N 9/90* (2013.01); *C07K 14/62* (2013.01); *C07K 14/65* (2013.01); *C07K 14/61* (2013.01); *C07K 14/655* (2013.01); *C07K 14/585* (2013.01); *C07K 2319/20* (2013.01); *C07K 14/4703* (2013.01); *C07K 14/005* (2013.01); *C07K 14/635* (2013.01); *C07K 2319/01* (2013.01); *C07K 14/56* (2013.01); *C07K 2319/21* (2013.01); *C12N 2740/16122* (2013.01); *C12N 15/70* (2013.01); *C07K 14/535* (2013.01); *C07K 14/505* (2013.01); *C07K 14/755* (2013.01); *G06Q 99/00* (2013.01); *C07K 14/605* (2013.01)

USPC ........ 530/413; 435/69.7; 435/71.1; 435/71.2; 530/402

(58) Field of Classification Search
CPC .......... C12P 21/00; C07K 1/22; C07K 1/107; C07K 17/00; C07K 17/02; C07K 17/10; C07K 17/12; C07K 2319/00; C07K 2319/20–2319/24
USPC ........ 530/413, 402, 345; 435/69.7, 71.1, 71.2
See application file for complete search history.

(56) References Cited

U.S. PATENT DOCUMENTS

| | | | | |
|---|---|---|---|---|
| 4,745,178 | A | * | 5/1988 | DiMarchi et al. .............. 530/345 |
| 5,648,244 | A | * | 7/1997 | Kuliopulos et al. .......... 435/69.7 |
| 5,739,281 | A | * | 4/1998 | Thogersen et al. ........... 530/350 |
| 5,834,247 | A | | 11/1998 | Comb et al. |
| 7,662,913 | B2 | | 2/2010 | Decarolis et al. |
| 7,820,409 | B2 | | 10/2010 | Maiti et al. |
| 7,829,311 | B2 | | 11/2010 | Decarolis et al. |
| 2003/0219854 | A1 | | 11/2003 | Guarna et al. |
| 2006/0269980 | A1 | * | 11/2006 | Gibbs ............................. 435/23 |
| 2007/0128622 | A1 | * | 6/2007 | Maiti et al. ........................ 435/6 |
| 2008/0096245 | A1 | | 4/2008 | Decarolis et al. |

FOREIGN PATENT DOCUMENTS

| | | |
|---|---|---|
| CN | 1786165 A | 6/2006 |
| WO | WO 2009/066320 A2 | 5/2009 |

OTHER PUBLICATIONS

Lischwe et al., "N-Chlorosuccinimidel/Urea Cleavage of Tryptophan Peptide Bonds", J. Biol. Chem. 252:4976-4980, 1977.*
Daenke et al., J. Gen. Virol. 75:2233-2239, 1994.*
Tee et al., J. Org. Chem. 59:7602-7608, 1994.*
Lundblad, R., "Chemical Regents for Protein Modification", pp. 247-251, CRC Press, New York, 2005.*
International search report and written opinion dated Jan. 20, 2011 for PCT/US2010/055946.
Yonemoto, et al. A general strategy for bacteria expression of amyloidogenic peptides using BCL-XL-1/2 fusions. Protein Sci. Sep. 2009;18(9):1978-86.
European search report and search opinion dated May 21, 2013 for EP Application No. 10829265.
Forsberg, et al. Comparison of two chemical cleavage methods for preparation of a truncated form of recombinant human insulin-like growth factor I from a secreted fusion protein. Biofactors. Dec. 1989;2(2):105-12.
Forsberg, et al. Separation and characterization of modified variants of recombinant human insulin-like growth factor I derived from a fusion protein secreted from *Escherichia coli*. Biochem. J. 1990; 271:357-363.

(Continued)

*Primary Examiner* — David J Steadman
(74) *Attorney, Agent, or Firm* — Wilson Sonsini Goodrich & Rosati

(57) ABSTRACT

The present invention relates to processes for the production of peptides, and the peptides produced accordingly. Peptides produced according to the invention may be produced more efficiently than peptides produced according to prior art processes. The production process of the invention may lead to advantages in yield, purity, and/or price. Methods of marketing peptides are also disclosed.

25 Claims, 13 Drawing Sheets

(56) References Cited

OTHER PUBLICATIONS

Mancuso, et al. Activated dimethyl sulfoxide: Useful reagents for synthesis. Synthesis 1981; 1981(3): 165-185. DOI: 10.1055/s-1981-29377.

Smith. Chemical Cleavage of Proteins at Tryptophan Residues. From: The Protein Protocols Handbook. Edited by: J. M. Walker Humana Press Inc., Totowa, NJ. 2009; 3rd ed. p. 375-380.

Tojo, et al. Oxidation of Alcohols to Aldehydes and Ketones: A guide to Current Common Practice. Springer. 2006; 97-179.

* cited by examiner

FIGURE 4

A. SEQ ID NO.: 1

1 mskqesqpdv qflarfsdaw nrhdidalmd fmadecefha vagpdlmgrs fvgreavreg
61 fqlawqafpd aawvdgehfv qgtrgvsest fkgtkadglr vearmvdvft frdgkiavkn
121 ayrkdrppva is

B. SEQ ID NO.: 2

1 mksiankene vaiihkliee yanaardkdi dkimshyapd irsfdaysql qfkgaddyrk
61 hwqtclsfcp gpsvfevhql etivdnnlav syyltycggt nekgetqggw mrgtmvhckm
121 ngkwkimheh ysipfdmktg ntlfdlkp

C. SEQ ID NO.: 3

1 mnnttrqdet airqlhdafe qaigakdldr imaqyapdvv afdavgalqf kgvaeyrahw
61 qrcfefcqge gffethelhv dvggelacsr mlthcggpna egemqtawmr gtrvwarrdg
121 ewkvihehfs mpfdmetgqv cmsstpsatq qvg

D. SEQ ID NO.: 4

1 htpehitavv qrfvaalnag dldgivalfa ddatvedp vgseprsgta airefyansl
61 klplaveltq evravaneaa faftvsfeyq grktvvapid hfrfngagkv vsiralfgek
121 nihacq

FIGURE 5

SEQ ID NO.: 5
CAT ACC CCA GAA CAC ATC ACC GCC GTG GTA CAG CGC TTT GTG GCT GCG CTC AAT GCCGGC GAT CTG GAC GGC ATC GTC GCG CTG TTT GCC GAT GAC GCC ACG GTG GAA GAC CCCGTG GGT TCC GAG CCC AGG TCC GGT ACG GCT GCG ATT CGT GAG TTT TAC GCC AAC TCGCTC AAA CTG CCT TTG GCG GTG GAG CTG ACG CAG GAG GTA CGC GCG GTC GCC AAC GAAGCG GCC TTC GCT TTC ACC GTC AGC TTC GAG TAT CAG GGC CGC AAG ACC GTA GTT GCGCCC ATC GAT CAC TTT CGC TTC AAT GGC GCC GGC AAG GTG GTG AGC ATC CGC GCC TTGTTT GGC GAG AAG AAT ATT CAC GCA TGC CAG CTC GAG

FIGURE 13

| Material | Vendor | Amount | Total Cost | 1L culture (amt) | 1L culture (cost) |
|---|---|---|---|---|---|
| KSI-His sequence | GenScript | 4 ug | $195 | reusable | $195 |
| Aβ(1-42) sequence | GenScript | 4 ug | $195 | N/A | $195 |
| LB Medium | Affymetrics | 1 kg | $520 | 25 g | $13 |
| Ampicillin | Sigma-Aldrich | 50 g | $100 | 100 mg | $0.20 |
| L-arabinose | Acros Organics | 25 g | $44 | 2 g | $3.50 |
| IPTG | GokiBio | 100 g | $309 | 250 mg | $0.80 |
| Tris Buffer | Fisher Scientific | 1 kg | $117 | 660 mg | $0.08 |
| NaCl | Fisher Scientific | 2.5 kg | $148 | 640 mg | $0.04 |
| Glycerol | Fisher Scientific | 4 L | $580 | 10 mL | $14.50 |
| PMSF | Fisher Scientific | 10 g | $90 | 50 mg | $0.45 |
| Triton-X 100 | Fisher Scientific | 100 g | $16 | 1 g | $0.16 |
| Bovine Serum Albumin | Biopharm Labs | 100 g | $155 | 1 mg | $0.002 |
| Acetic Acid (glacial) | ScienceLab | 4 L | $69 | 10 mL | $0.17 |
| N-Acetyl methionine | Sigma-Aldrich | 5 g | $35 | 100 mg | $0.70 |
| NBS | TCI America | 25 g | $10 | 100 mg | $0.04 |
| TALON Resin | Clontech | 1 L | $560 | 1 L (reusable) | $560 |
| | | | TOTAL COST/L β-Amyloid 1-42 | | $229.00 |
| | | | g/L β-Amyloid 1-42 | | 2 g |
| | | | TOTAL COST/mg β-Amyloid 1-42 | | $0.11 |

EFFICIENT PRODUCTION OF PEPTIDES

CROSS-REFERENCE TO RELATED APPLICATIONS

This application claims priority from U.S. Provisional Application 61/259,367, filed Nov. 9, 2009, the entire contents of which are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Jan. 5, 2011, is named AmideBioSeqList.txt and is 9 Kilobytes in size.

FIELD OF THE INVENTION

The present invention relates to processes for the production of peptides, and the peptides produced accordingly. Peptides produced according to the invention may be produced more efficiently than peptides produced according to prior art processes. The production process of the invention may lead to advantages in yield, purity, and/or price. Methods of marketing peptides are also disclosed.

BACKGROUND OF THE INVENTION

Peptides are becoming increasingly useful in basic research and clinical practice. Interest in peptides can be attributed to their role as mediators in many biological pathways and to their unique intrinsic properties. For example, many peptides have high specificity for their target with low non-specific binding to molecules that are not targeted, thus minimizing drug-drug interactions, and many peptides show low accumulation in tissues over time, thus reducing side effects. Moreover, peptides are often broken down in vivo to their constituent amino acids, thus reducing the risk of complications due to toxic metabolic intermediates.

Peptide market values are generally grouped within five broad categories in the life sciences field: cytokines, enzymes, hormones, monoclonal antibodies, and vaccines. According to a 2008 Frost & Sullivan market research report, these broad categories can be further subdivided in the United States into vaccines (34%), monoclonal antibodies (30%), recombinant hormones and proteins (10%), gene therapy (6%), cell therapy (4%), antisense (3%), interferons (3%), interleukins (2%), growth factors (1%), and others (7%). Each of these categories is undergoing high growth rates. For example, from 2004 to 2007, the monoclonal antibody market alone almost doubled its revenue from $6.3 billion to $12.6 billion. In addition, several new products, including Bydureon® (exenatide LAR for diabetes; Amylin/Eli Lilly), Extavia® (interferon beta-1b for multiple sclerosis; Novartis), and Simponi™ (golimumab for rheumatoid and psoriatic arthritis; Centocor) have been approved recently by the FDA.

Moreover, peptide markets are likely to continue to grow. For example, of 633 drugs in development in 2008, nearly half were peptides. Analysts estimate an eight percent compound annual growth rate over the next half-decade resulting in a potential $20 billion in earnings for the year 2013, representing nearly fifteen percent of the forecast total earnings for the biopharmaceuticals market. Additional opportunities exist for peptides as reagents in basic research and diagnostic platforms.

While advances in the field of peptide science have led to impressive commercial growth, several barriers remain to be overcome. For example, peptides tend to have delivery and stability problems compared to traditional small molecule therapeutics. Attempts to address these problems have involved oral, nasal, and pulmonary delivery. However, these attempts often require higher doses of the peptides or yield unfavorable pharmacokinetic profiles.

One of the biggest barriers to increased use of peptides is the cost of the peptides themselves, which is generally significantly higher than the cost of producing small molecule therapeutics. For instance, Nutropin AQ®, a form of recombinant human growth hormone manufactured by Genentech and administered to patients with growth defects during adolescence, costs $30,000 annually. High prices are an even bigger barrier to obtaining peptides when the peptide is used for research purposes. For example, β-amyloid (1-42) peptide is a research peptide with strong implications in the onset of Alzheimer's disease. A survey of prices from various peptide manufacturers finds the price of research-grade β-amyloid (1-42) ranging from $225/mg ($21^{st}$ Century Biochemicals) to $1,490/mg (Sigma-Aldrich), with the typical price at $300-$320/mg (AnaSpec, California Peptide, Innovagen, rPeptide) (estimated 2009 prices as obtained from catalogs).

Due to the importance of peptides and their high price, there is a persistent and long-felt yet unfulfilled need for lowering the cost of peptides. The industrial and medical use of peptides has created a need for an improved means of production and purification, where the improvement may be in efficiency, price, and/or quality of product. Accordingly, the present invention is directed to processes for the production of peptides, and the peptides produced. Methods of marketing peptides are also disclosed.

SUMMARY OF THE INVENTION

In various embodiments, the invention is directed to a method for producing a target peptide. According to the method of the invention, a fusion peptide is produced comprising an affinity tag, a cleavable tag, and the target peptide, followed by binding of the fusion peptide to an affinity material, cleaving the fusion peptide to release the target peptide; and removing the target peptide from the affinity material. In general, following binding of the fusion peptide to an affinity material, the affinity material is washed to remove unbound material. Moreover, following removal of the target peptide from the affinity material, the target peptide may be further modified or packaged for distribution.

The target peptide is not limited, and may include a wide variety of peptides. For example, in various embodiments, the target peptide is selected from the group consisting of amyloid beta, calcitonin, enfuvirtide, epoetin, epoetin delta, erythropoietin, exenatide, factor VIII, factor X, glucocerebrosidase, glucagon-like peptide-1 (GLP-1), granulocyte-colony stimulating factor (G-CSF), human growth hormone (hGH), insulin, insulin A, insulin B, insulin-like growth factor 1 (IGF-1), interferon, liraglutide, somatostatin, teriparatide, and tissue plasminogen activator (TPA). In various embodiments, the target peptide is selected from amyloid beta, enfuvirtide, exenatide, insulin, and teriparatide.

The fusion peptide may be produced in a variety of methods. In one embodiment, the fusion peptide is produced in a bacterial expression system, such as an E. coli expression system. In alternate embodiments, the expression system is a yeast expression system or a mammalian expression system.

In various embodiments, the fusion peptide according to the invention further comprises an inclusion-body directing peptide. In such embodiments, prior to the binding of the fusion peptide to the affinity material, the fusion peptide may be isolated from the expression system by separation of inclusion bodies from the remainder of the cell in the expression system. Following initial isolation, the fusion peptide may be solubilized to allow further handling. In various embodiments, the inclusion-body directing peptide is selected from the group consisting of inclusion-body directing peptide is a ketosteroid isomerase, an inclusion-body directing functional fragment of a ketosteroid isomerase, an inclusion-body directing functional homolog of a ketosteroid isomerase, a BRCA2 peptide, an inclusion-body directing functional fragment of BRCA2, or an inclusion-body directing functional homolog of BRCA2.

In various embodiments, the affinity tag is selected from the group consisting of poly-histidine, poly-lysine, poly-aspartic acid, or poly-glutamic acid. Moreover, the cleavable tag may be selected from the group consisting of Trp, His-Met, Pro-Met, and an unnatural amino acid. In the event of more than one cleavable tag in the fusion peptide, the various cleavable tags may be orthogonal, i.e. have different reactivity with any particular cleavage agent. In various embodiments, the cleaving step is performed with an agent selected from the group consisting of NBS, NCS, or Pd(H2O)4.

Methods according to the invention are also directed to evaluating the commercial market for a target peptide comprising a) producing a target peptide according to the methods described herein; b) making sample amounts of the target peptide available for no cost or minimal cost; and c) measuring the number of requests for the target peptide over a period of time.

In addition to the above methods, the invention is directed to the target peptide produce according to the invention, in particular to target peptides of greater than 99% purity. Also, vectors for use in expression systems for the production of target peptides according to the invention are envisioned. For example, vectors according to the invention may include a nucleotide sequence encoding an affinity tag; a nucleotide sequence encoding a cleavable tag; and a nucleotide sequence encoding a target peptide; wherein the nucleotides are arranged in operable combination and further wherein expression of the operable combination results in a fusion protein comprising an affinity tag, a cleavable tag, and a target peptide. Additional embodiments of the invention are directed to a cell comprising the vectors described herein as well as a fusion protein produced according to the methods described herein.

BRIEF DESCRIPTION OF THE DRAWINGS

Various features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4A-D presents four embodiments of amino acid sequences for ketosteroid isomerase.

FIG. 5 presents one embodiment of a nucleic acid sequence for ketosteroid isomerase.

In FIG. 9, Z-Trp-Y is cleaved at the carboxy terminus of the Trp residue to yield a modified Z-Trp and a free amino group on Y (i.e., $H_2N$—Y).

FIG. 13 presents an estimated manufacturing cost analysis of direct materials used. Based on an average inclusion body preparation of 5 grams per liter, a 50% cleavage success rate, and product loss during purification, the materials to synthesize beta-amyloid (1-42) cost only $0.11 per milligram.

DETAILED DESCRIPTION OF THE INVENTION

Figure 1:
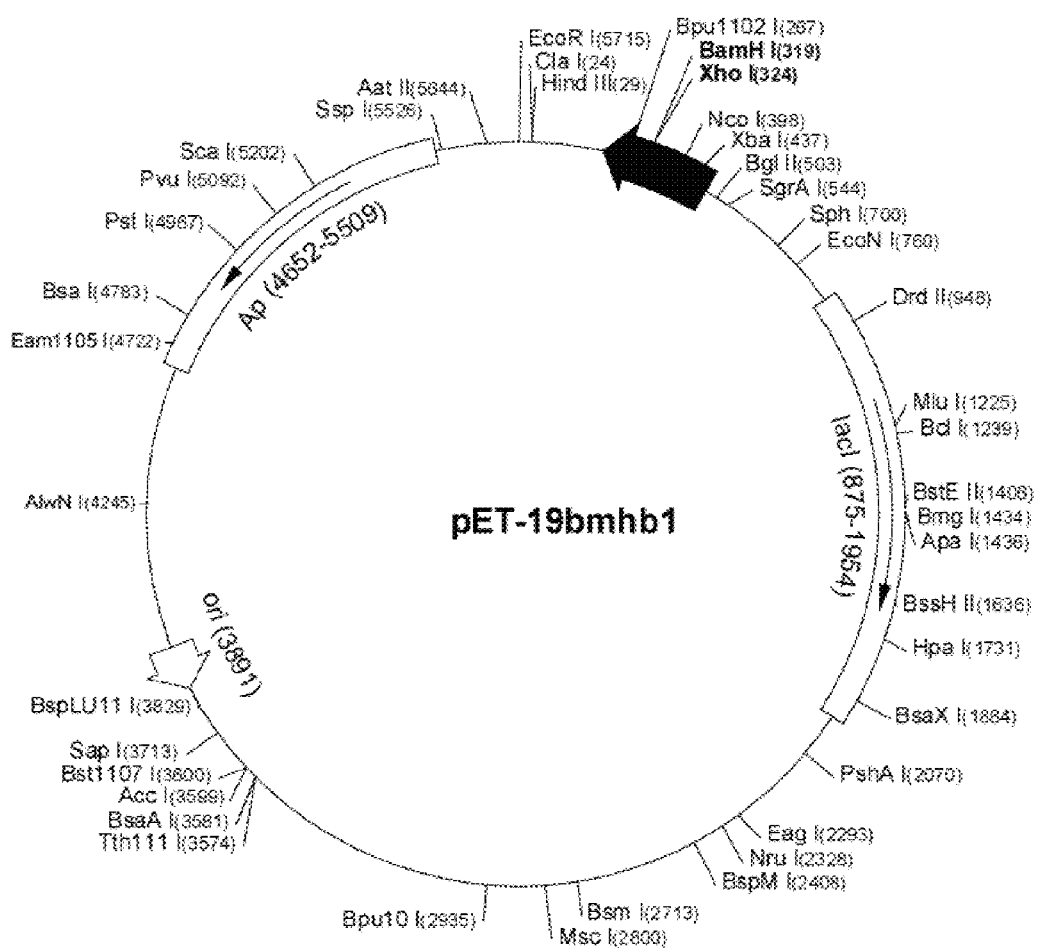
FIG. 1 diagrams a modified form of the commercially available pET-19b vector (pET-19bmhb1). Such vectors can be used to produce a KSI sequence flanked by two NcoI restriction sites and a histidine tag—tryptophan-β-amyloid (1-42) sequence flanked by two XhoI restriction sites.

The present invention provides methods for producing fusion peptides that can be purified and cleaved into desired peptides, and the peptides produced according to the methods. In various embodiments, the method of the invention includes induction, inclusion body isolation, affinity column purification, and chemical cleavage. In various embodiments, the present invention utilizes an expression vector to make the peptides according to the invention. In some aspects, by combining molecular expression technologies that employ genetically-malleable microorganisms such as E. coli cells to synthesize a peptide of interest with post-expression isolation and modification, one can synthesize a desired peptide rapidly and efficiently. In various embodiments, the invention concerns production of fusion peptides that can be purified using affinity separation and cleaved with a chemical reagent to release a target peptide.

In various embodiments, the invention is directed to a vector that encodes an inclusion body targeting sequence, an affinity tag to facilitate purification, and a specific amino acid sequence that facilitates selective chemical cleavage. Variously, the inclusion body targeting amino acid sequence comprises between 1 and 125 amino acids of a ketosteroid isomerase protein. The affinity tag sequence may comprise a poly-histidine, a poly-lysine, poly-aspartic acid, or poly-glutamic acid. In one embodiment, the vector further comprises an expression promoter located on the 5' end of the affinity tag sequence. In one embodiment, the invention is directed to a vector that codes for a specific sequence that facilitates selective chemical cleavage to yield a peptide of interest following purification. Such chemically cleavable amino acid sequences include Trp, His-Met, or Pro-Met.

In one embodiment, the present invention contemplates a peptide expression vector, comprising: a) a first nucleotide sequence encoding an affinity tag amino acid sequence; b) a second nucleotide sequence encoding an inclusion body targeting amino acid sequence; c) a third nucleotide sequence encoding a chemically cleavable amino acid sequence; and d) a promoter in operable combination with the first, second, and third nucleotide sequences.

In one embodiment, the present invention contemplates a method for producing a peptide of commercial or therapeutic interest comprising the steps of: a) cleaving a vector with a restriction endonuclease to produce a cleaved vector; b) ligating the cleavage site to one or more nucleic acids, wherein the nucleic acids encode a desired peptide having at least a base overhang at each end configured and arranged for ligation with the cleaved vector to produce a second vector suitable for expression of a fusion peptide; c) transforming the second vector into suitable host cell; d) incubating the host cell under conditions suitable for expression of the fusion peptide; e) isolation of inclusion bodies from the host cell; f) solubilization and extraction of the fusion peptide from the inclusion bodies; g) binding of the fusion peptide to a suitable affinity material; h) washing of bound fusion peptide to remove impurities; and i) cleaving the fusion peptide to release the said target peptide.

Peptides produced by the methods of the invention may have significantly lower costs and/or other advantageous features. These potentially cheaper costs may lie not only in less expensive raw materials required for synthesis, but also may lie in less chemical waste which is generated compared to the traditional process of solid phase peptide synthesis, or in more efficient processing to achieve a certain purity, thus lowering the cost of the material. Furthermore, the exclusion of a waste stream may be particularly beneficial to the environment. In various embodiments, processes according to the invention provide a high yield of peptide with high purity. In various embodiments, peptides produced according to the invention may be R&D grade peptides or clinical grade therapeutics.

DEFINITIONS

Unless defined otherwise, all technical and scientific terms used herein have the same meaning as commonly understood by a person of ordinary skill in the art.

As used herein, the term "peptide" is intended to mean any polymer comprising amino acids linked by peptide bonds. The term "peptide" is intended to include polymers that are assembled using a ribosome as well as polymers that are assembled by enzymes (i.e., non-ribosomal peptides) and polymers that are assembled synthetically. In various embodiments, the term "peptide" may be considered synonymous with "protein," or "polypeptide." In various embodiments, the term "peptide" may be limited to a polymer of greater than 50 amino acids, or alternatively, 50 or fewer amino acids. In various embodiments, the term "peptide" is intended to include only amino acids as monomeric units for the polymer, while in various embodiments, the term "peptide" includes additional components and/or modifications to the amino acid backbone. For example, in various embodiments, the term "peptide" may be applied to a core polymer of amino acids as well as derivatives of the core polymer, such as core polymers with pendant polyethylene glycol groups or core polymers with amide groups at the amino or carboxy terminus of the amino acid chain.

As used herein, "consisting essentially of" may exclude those features not listed herein that would otherwise alter the operation of the invention. However, the use of the phrase "consisting essentially of" does not exclude features that do not alter the operation of the required components.

The term "polymer" is a molecule (or macromolecule) composed of repeating structural units connected by covalent chemical bonds.

A "patient," "subject" or "host" to be treated with the composition of the present invention may mean either a human or non-human animal. The term "mammal" is known in the art, and exemplary mammals include humans, primates, bovines, porcines, canines, felines, and rodents (e.g., mice and rats).

I. Target Peptides

The methods of the invention are applicable to a wide range of peptides as the isolated product, which may be referred to as target peptides. Peptides produced according to the methods of the invention may be naturally-occurring peptides, non-naturally-occurring peptides, or naturally-occurring peptides with non-natural substitutions, deletions, or additions. In various embodiments, the target peptide may be modified chemically or biologically following isolation to yield a derivative of the target peptide, such as a target peptide with one or more carboxamide groups in place of free carboxy groups.

In various embodiments, the peptide is selected from vaccines, antibodies, recombinant hormones and proteins, interferons, interleukins, and growth factors. In some embodiments, the target peptide is fifty or fewer amino acids. In some embodiments, the target peptide is greater than fifty amino acids.

Further non-limiting embodiments of the invention include peptides and analogs thereof selected from the group consisting of angiotensin, arginine vasopressin (AVP), AGG01, amylin (IAPP), amyloid beta, N-acetylgalactosamine-4-sulfatase (rhASB; galsulfase), avian pancreatic polypeptide (APP), B-type natriuretic peptide (BNP), calcitonin peptides, calcitonin, colistin (polymyxin E), colistin copolymer 1 (Cop-1), cyclosporin, darbepoetin, PDpoetin, dornase alfa, eledoisin, β-endorphin, enfuvirtide, enkephalin pentapeptides, epoetin, epoetin delta, erythropoietin, exenatide, factor VIII, factor X, follicle-stimulating hormone (FSH), alpha-galactosidase A (Fabrazyme), Growth Hormone Releasing Hormone 1-24 (GHRH 1-24), β-globin, glucagon, glucocerebrosidase, glucagon-like peptide-1 (GLP-1), granulocyte-colony stimulating factor (G-CSF), granulocyte macrophage-colony stimulating factor (GM-CSF), growth hormone, Hepatitis B viral envelope protein, human growth hormone (hGH), insulin, insulin A, insulin B, insulin-like growth factor 1 (IGF-1), interferon, kassinin, alpha-L-iduronidase (rhIDU; laronidase), lactotripeptides, leptin, liraglutide (NN2211, VICTOZA), luteinizing-hormone-releasing hormone, methoxy polyethylene glycol-epoetin beta (MIRCERA), myoglobin, neurokinin A, neurokinin B, NN9924, NPY (NeuroPeptide Y), octreotide, pituitary adenylate cyclase activating peptide (PACAP), parathyroid hormone (PTH), Peptide Histidine Isoleucine 27 (PHI 27), proopiomelanocortin (POMC) peptides, prodynorphin peptides, polymyxins, polymyxin B, Pancreatic Polypeptide (PPY), Peptide YY (PYY), secretin, somatostatin, Substance P, teriparatide (FORTEO), tissue plasminogen activator (TPA), thrombospondins (TSP), ubiquitin, urogastrone, Vasoactive Intestinal Peptide (VIP, or PHM27), and viral envelope proteins. In various embodiments, the target peptide is selected from amyloid beta, calcitonin, enfuvirtide, epoetin, epoetin delta, erythropoietin, exenatide, factor VIII, factor X, glucocerebrosidase, glucagon-like peptide-1 (GLP-1), granulocyte-colony stimulating factor (G-CSF), human growth hormone (hGH), insulin, insulin A, insulin B, insulin-like growth factor 1 (IGF-1), interferon, liraglutide, somatostatin, teriparatide, and tissue plasminogen activator (TPA). In various embodiments, the target peptide is selected from amyloid beta and insulin.

In various embodiments, the target peptide is a hormone. For example, in various embodiments, the target peptide is selected from the group consisting of Activin, inhibin, Adiponectin, Adipose derived hormones, Adrenocorticotropic hormone, Afamelanotide, Agouti signalling peptide, Allatostatin, Amylin, Angiotensin, Atrial natriuretic peptide, Bovine somatotropin, Bradykinin, Brain-derived neurotrophic factor, CJC-1295, Calcitonin, Ciliary neurotrophic factor, Corticotropin-releasing hormone, Cosyntropin, Endothelin, Enteroglucagon, Follicle-stimulating hormone, Gastrin, Gastroinhibitory peptide, Glucagon, Glucagon hormone family, Glucagon-like peptide-1, Gonadotropin, Granulocyte colony-stimulating factor, Growth hormone, Growth hormone releasing hormone, Hepcidin, Human chorionic gonadotropin, Human placental lactogen, Incretin, Insulin, Insulin glargine, Insulin lispro, Insulin aspart, Insulin-like growth factor 2, Insulin-like growth factor, Leptin, Liraglutide, Luteinizing hormone, Melanocortin, Melanocyte-stimulating hormone, Melanotan II, Minigastrin, N-terminal prohormone of brain natriuretic peptide, Nerve growth factor, Neurotrophin-3, NPH insulin, Obestatin, Orexin, Osteocalcin, Pancreatic hormone, Parathyroid hormone, Peptide YY, Peptide hormone, Plasma renin activity, Pramlintide, Preprohormone, Proislet Amyloid Polypeptide, Prolactin, Relaxin, Renin, Salcatonin, Secretin, Sincalide, Teleost leptins, Thyroid-stimulating hormone, Thyrotropin-releasing hormone, Urocortin, Urocortin II, Urocortin III, Vasoactive intestinal peptide, and Vitellogenin.

In various embodiments, the target peptide is already commercially available through a production process that differs from the process according to the invention. While not wishing to be bound by theory, it is believed that peptides produced according to the present invention will have differing levels of residual components from the process of production. For example, in comparison with peptides of the same sequence produced according to conventional recombinant processes, peptides produced according to the present invention may be expected to have fewer residual cellular contaminants upon initial purification. Alternatively, in comparison with peptides of the same sequence produced by conventional synthetic processes, peptides produced according to the present invention may be expected to have fewer residual chemical contaminants upon initial purification. Various commercially available peptides may be found in paper catalogs or in online catalogs, for example, from Sigma-Aldrich (<<sigmaaldrich.com/life-science/cell-biology/peptides-and-proteins.html>>), California Peptide (<<californiapeptide.com/peptide catalog table>>), CPCScientific (<<cpcscientific.com/products/browseCatalog.asp>>), and Bachem (<<shop.bachem.com/ep6sf/index.ep>>).

In various embodiments, target peptides do not include tryptophan in their sequence.

II. Inclusion-Body Directing Peptides

Inclusion bodies are composed of insoluble and denatured forms of a peptide and are about 0.5-1.3 μm in diameter. These dense and porous aggregates help to simplify recombinant protein production since they have a high homogeneity of the expressed protein or peptide, result in lower degradation of the expressed protein or peptide because of a higher resistance to proteolytic attack by cellular proteases, and are easy to isolate from the rest of the cell due to differences in their density and size relative to the other cellular components. In various embodiments, the presence of inclusion bodies permits production of increased concentrations of the expressed protein or peptide due to reduced toxicity by the protein or peptide upon segregation into an inclusion body. Once isolated, the inclusion bodies may be solubilized to allow for further manipulation and/or purification.

An inclusion-body directing peptide is an amino acid sequence that helps to direct a newly translated protein or peptide into insoluble aggregates within the host cell. Prior to final isolation, in various embodiments of the invention the target peptide is produced as a fusion peptide where the fusion peptide includes as part of its sequence of amino acids an inclusion-body directing peptide. The methods of the invention are applicable to a wide range of inclusion-body directing peptides as components of the expressed fusion protein or peptide.

In various embodiments, the inclusion-body directing peptide is a keto-steroid isomerase (KSI) sequence, a functional fragment thereof, or a functional homolog thereof.

In various embodiments, the inclusion-body directing peptide is a BRCA-2 sequence, a functional fragment thereof, or a functional homolog thereof.

III. Affinity-Tag Peptides

According to the invention, a wide variety of affinity tags may be used. Affinity tags useful according to the invention may be specific for cations, anions, metals, or any other material suitable for an affinity column. In one embodiment, any peptide not possessing an affinity tag will elute through the affinity column leaving the desired fusion peptide bound to the affinity column via the affinity tag.

Specific affinity tags according to the invention may include poly-lysine, poly-histidine, poly-glutamic acid, or poly-arginine peptides. For example, the affinity tags may be 5-10 lysines, 5-10 histidines, 5-10 glutamic acids, or 5-10 arginines. In various embodiments, the affinity tag is a hexa-histidine sequence, hexa-lysine sequence, hexa-glutamic acid sequence, or hexa-arginine sequence. Alternatively, the HAT-tag (Clontech) may be used. In various embodiments, the affinity tag is a His-Trp Ni-affinity tag.

Without wishing to be bound by theory, it is believed that the histidine residues of a poly-histidine tag bind with high affinity to Ni-NTA or TALON resins. Both of these resins contain a divalent cation (Ni-NTA resins contain $Mg^{2+}$; TALON resins contain $Co^{2+}$) that forms a high affinity coordination with the His tag.

In various embodiments, the affinity tag has a pI (isoelectric point) that is at least one pH unit separate from the pI of the target peptide. Such difference may be either above or below the pI of the target peptide. For example, in various embodiments, the target peptide has a high pI, and the affinity tag has a pI that is at least one pH unit lower, at least two pH units lower, at least three pH units lower, at least four pH units lower, at least five pH units lower, at least six pH units lower, or at least seven pH units lower. Alternatively, the target peptide has a low pI, and the affinity tag has a pI that is at least one pH unit higher, at least two pH units higher, at least three pH units higher, at least four pH units higher, at least five pH units higher, at least six pH units higher, or at least seven pH units higher. In one embodiment, the target peptide has a pI of about 10 and the affinity tag has a pI of about 6.

In various embodiments, the affinity tag is contained within the native sequence of the inclusion body directing peptide. Alternatively, the inclusion body directing peptide is modified to include an affinity tag. For example, in one embodiment, the affinity tag is a KSI or BRCA2 sequence modified to include extra histidines, extra lysines, extra arginines, or extra glutamic acids.

In various embodiments, epitopes may be used such as FLAG (Eastman Kodak) or myc (Invitrogen) in conjunction with their antibody pairs.

IV. Cleavable Tags

The methods of the invention are applicable to a wide range of cleavable tags.

In various embodiments, the cleavable tag is a tryptophan at the amino terminus of the target peptide. Upon cleavage with a cleaving agent, the amide bond connecting the tryptophan to the target peptide is cleaved, and the target peptide is released from the affinity column.

In various embodiments, the cleavable tag is a tryptophan at the amino terminus of the target peptide, where the cleavable tag also includes an amino acid with a charged side-chain in the local environment of the tryptophan, such as within five amino acids on the upstream (i.e. amino) or downstream (i.e. carboxy) side of the tryptophan. In various embodiments, the presence of an amino acid side-chain within five amino acids on the amino terminus of the tryptophan amino acid allows for selectivity of cleavage of the tryptophan of the cleavable tag over any other tryptophans that may be present in the fusion peptide, for example, tryptophans as part of the inclusion body directing peptide or as part of the target peptide. For example, in various embodiments, an amino acid with a positively charged side chain such as lysine, ornithine, or arginine is within five, four, three, or two amino acid units, or is adjacent on the amino terminus to the tryptophan of the cleavable tag. In various embodiments, a glutamic acid amino acid is within five, four, three, or two amino acid units, or is adjacent on the amino terminus to the tryptophan of the cleavable tag.

In various embodiments, the cleavable tag is His-Met, or Pro-Met.

Figure 12:
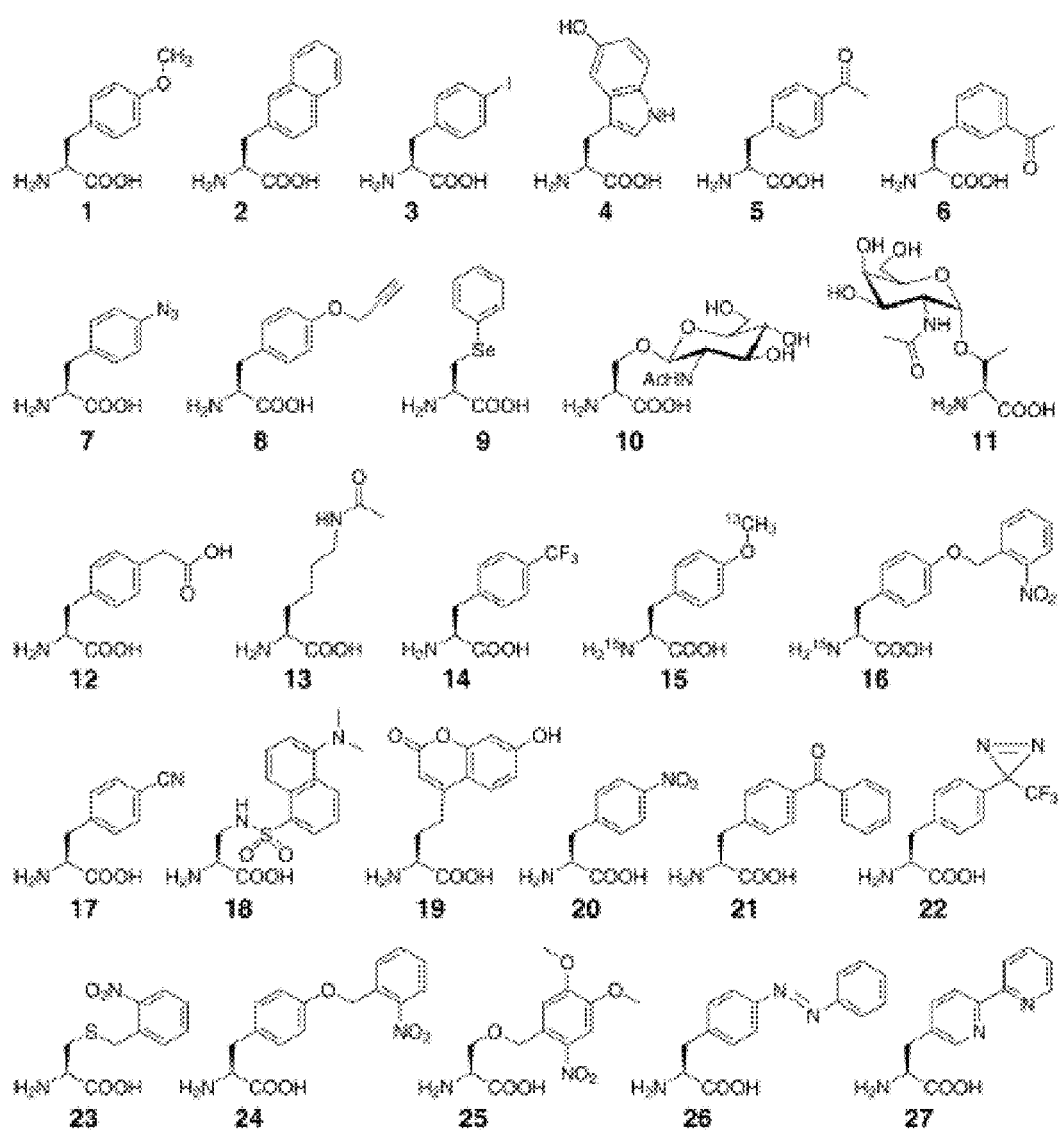
FIG. 12 presents the chemical structures of a variety of unnatural amino acids that have been incorporated into peptides and proteins by cell systems through genetic modification of the cell systems. See Wang, et al., (2009) Chem. Biol. 16(3):323-36.

In various embodiments, the cleavable tag is an unnatural amino acid. Cells have been modified to enable the cells to produce peptides which contain unnatural amino acids. For instance, Wang, et al., (2001) Science 292:498-500, describes modifications made to the protein biosynthetic machinery of E. coli which allow the site-specific incorporation of an unnatural amino acid, O-methyl-L-tyrosine, in response to an amber stop codon (TAG). Wang, et al., (2009) Chem. Biol. 16(3):323-36 provides a review of numerous unnatural amino acids that have been site-specifically incorporated into proteins in E. coli, yeast, or mammalian cells. Without wishing to be bound by theory, it is believed that incorporation of one or more unnatural amino acids can provide additional selectivity for cleavage at the unnatural amino acid over non-specific cleavage at other sites on the fusion peptide. In various embodiments, the unnatural amino acid is selected from compounds 1-27 in FIG. 12.

In some aspects, the present invention includes the production of fusion peptides comprising unnatural amino acids. In some aspects, prokaryotic cells with modifications to the protein biosynthetic machinery produce such fusion peptides. Examples of such prokaryotic cells include E. coli. In some aspects the modifications comprise adding orthogonal tRNA/synthetase pairs. In some aspects four base codons encode novel amino acids. In some aspects, E. coli allow the site-specific incorporation of the unnatural amino acid O-methyl-L-tyrosine into a peptide in response to an amber stop codon (TAG) being included in an expression vector.

V. Fusion Peptide Synthesis

Numerous methods for producing peptides may be adapted to the invention. Various methods are described in detail herein.

A. Ribosomal Synthesis

In various embodiments, peptides may be produced by ribosomal synthesis, which utilizes the fundamental methods of transcription and translation to express peptides. Ribosomal synthesis is usually performed by manipulating the genetic code of various expression systems. Some peptides can be expressed in their native form in eukaryotic hosts such as Chinese hamster ovary (CHO) cells Animal cell culture may require prolonged growing times to achieve maximum cell density and may achieve lower cell density than prokaryotic cell cultures (see Cleland, J. (1993) ACS Symposium Series 526, Protein Folding In Vivo and In Vitro, American Chemical Society). Bacterial host expression systems such as Escherichia coli may achieve higher productivity than animal cell culture, and may have fewer regulatory hurdles for peptides intended to be used therapeutically. Numerous U.S. patents on general bacterial expression of recombinant proteins exist, including U.S. Pat. No. 4,565,785.

In one embodiment, the expression system is a microbial expression system. For example, in one embodiment, the process uses E. coli cells.

1. Construction of Vectors

In various embodiments, the method of the invention involves the construction of a DNA vector which includes certain selectable markers (such as antibiotic resistance in the case of E. coli) enabling selective screening against the cells that do not contain the constructed vector with the gene of interest. Vectors according to the invention may include hybrid promoters and multiple cloning sites for the incorporation of different genes. Various expression vectors may include the pET system and the pBAD system.

The pET system encompasses more than 40 different variations on the standard pET vector. In various embodiments, the pET system utilizes a T7 promoter that is recognized specifically by T7 RNA polymerase. This polymerase can transcribe DNA five times faster than *E. coli* RNA polymerase allowing for increased levels of transcription. In various embodiments, the *Escherichia coli* is protease deficient.

In one embodiment, a vector is designed with a sequences coding for a fusion peptide comprising an inclusion-body directing peptide, an affinity tag peptide, a cleavable peptide, and the target peptide. For example, in one embodiment, the vector is a pET-19b vector is modified to include a ketosteroid isomerase (KSI) sequence as the inclusion-body directing peptide. Thus, following cleavage of a restriction site such as the NcoI restriction site and insertion of the KSI sequence, the KSI sequence is flanked by two NcoI restriction sites. In addition, such a vector may be modified to include a histidine tag sequence as the sequence coding for an affinity tag adjacent to a tryptophan-encoding tag sequence as the sequence coding for a cleavable peptide which is further adjacent to a sequence coding for a target peptide such as the beta-amyloid (1-42) sequence. If an XhoI restriction site is used for purposes of insertion, the newly inserted sequence is flanked by two XhoI restriction sites. FIG. 1 diagrams one embodiment of a modified pET-19b (pET-19bmhb1) vector that can be used to produce a KSI sequence flanked by two NcoI restriction sites, and a histidine tag—tryptophan—beta-amyloid (1-42) sequence flanked by two XhoI restriction sites.

As such, a vector according to the invention such as a modified pET-19b vector contains the desired fusion peptide in a four part sequence: a KSI sequence or functional fragment to sequester the synthesized fusion protein into inclusion bodies, an affinity tag such as hexahistidine, a cleavage tag such as a tryptophan, and the target peptide.

2. Inoculation and Induction or Activation

Upon construction of an appropriate vector, the vector may be introduced into a host cell according to any method, and expression of the desired fusion peptide may be induced or activated by any method in the art.

In some embodiments once constructed, a vector according to the invention is inoculated or transformed into competent cells. In various embodiments, the competent cells may be mammalian cells such as Chinese hamster ovary cells, or microbial cells, such as *E. coli* cells. For example, the cells may be commercially available, such as DH5-α *E. coli* cells (available from Invitrogen).

In various embodiments, transformed cells can be plated onto agar containing an antibacterial agent to prevent the growth of any cells that do not contain a resistance gene, thereby selecting for cells that have been transformed. In some embodiments, transformed *E. coli* cells are plated onto agar containing ampicillin to prevent the growth of any *E. coli* strains that do not contain the constructed pET-19b vector, and a colony is selected for further expansion.

Colonies from the plating process may be grown in starter culture or broth according to standard cell culture techniques. For example, in some embodiments, one colony from an agar plate is grown in a starter culture of broth, which may optionally contain an antibacterial agent. Typically, cells are grown to a preselected optical density before being further processed to obtain fusion peptide. For example, cells may be grown to an optical density (OD) of 0.1, 0.2, 0.3, 0.4, 0.5, 0.6, 0.7, 0.8, or 0.9, all values being about. In some embodiments the cells are grown to an optical density (OD) of about 0.5.

In a bacterial expression system, once the vector-containing bacterial cells have been isolated, inducible transcription may be used to produce the desired fusion peptide. For example, in *E. coli* cells, the lac operon serves as an inducible promoter that is activated under certain environmental conditions. *E. coli* are always capable of metabolizing the monosaccharide glucose. However, in order to metabolize the disaccharide lactose, the cells need an enzyme known as β-galactosidase. Thus, low extracellular glucose concentrations and high lactose concentrations induce the lac operon and the gene for β-galactosidase is transcribed. Accordingly, in various embodiments, an inducible promoter such as the lac operon is situated upstream from the sequence coding for the fusion peptide. Upon induction of the lac operon, transcription of the sequence coding for the desired fusion peptide occurs.

Figure 2:
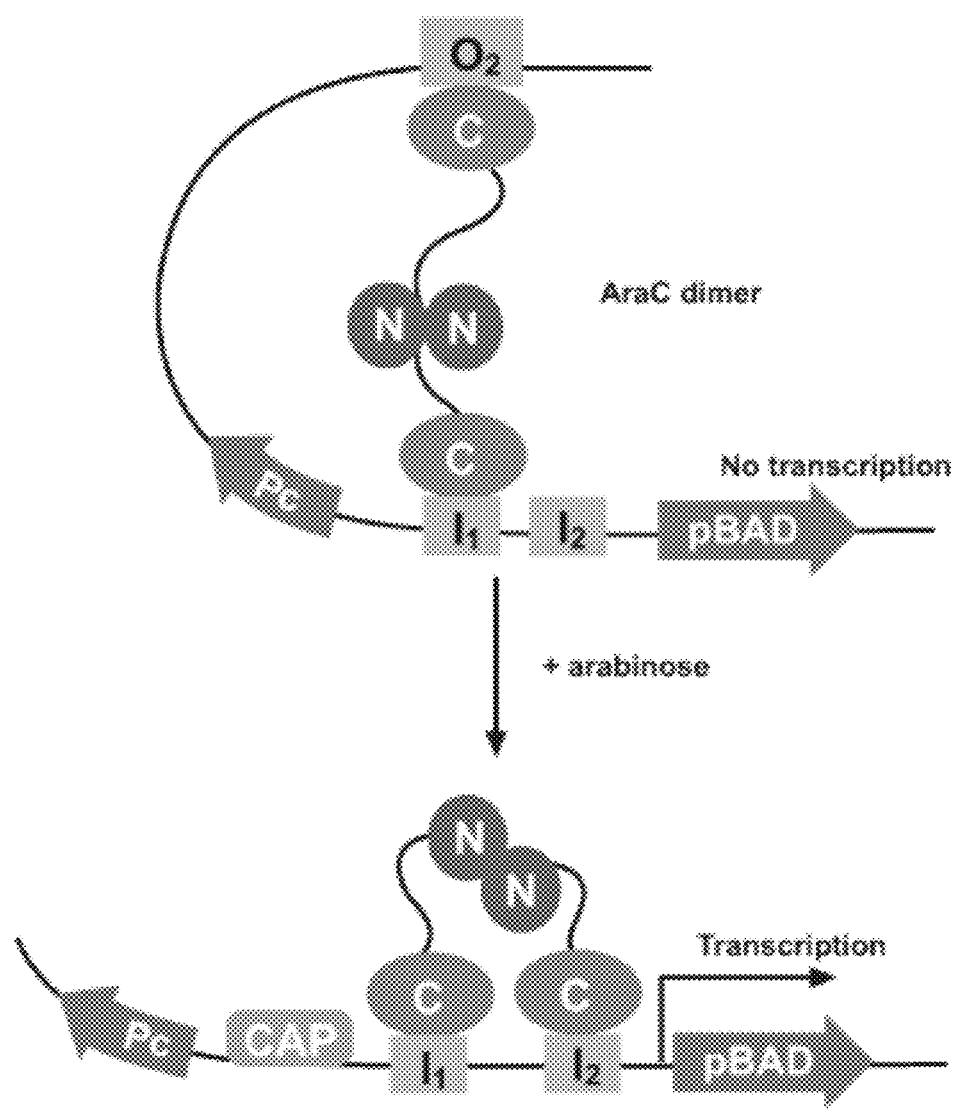
FIG. 2 illustrates activation of transcription in a commercially available pBAD promoter via the addition of L-arabinose. Arabinose binds to AraC ("C" in the diagram) and causes the protein to release the $O_2$ site and bind the $I_2$ site which is adjacent to the $I_1$ site. This releases the DNA loop and allows transcription to begin. A second level of control is present in the cAMP activator protein (CAP)-cAMP complex, which binds to the DNA and stimulates binding of AraC to $I_1$ and $I_2$. Basal expression levels can be repressed by introducing glucose to the growth medium, which lowers cAMP levels and in turn decreases the binding of CAP, thus decreasing transcriptional activation.

The term "activation" refers to the removal of repressor protein. A repressor protein is generally allosteric meaning it changes shape when bound by an inducer molecule and dissociates from the promoter. This dissociation allows for the transcription complex to assemble on DNA and initiate transcription of any genes downstream of the promoter. Therefore, by splicing genes produced in vitro into the bacterial genome, one can control the expression of novel genes. This trait may be used advantageously when dealing with inclusion bodies if the production and amassing of inclusion bodies becomes toxic enough to kill *E. coli*. For example, expression of the desired fusion peptide can be delayed until a sufficient population of cells has been cultured, and then the promoter can be induced to express a large amount of fusion peptide by removal of the repressor protein. Thus, the L-arabinose operon may be activated according to the invention for increased protein expression at a desired timepoint. Specifically, the L-arabinose operon may be activated by both the addition of L-arabinose into the growth medium and the addition of IPTG, a molecule that acts as an activator to dissociate the repressor protein from the operator DNA. FIG. 2 illustrates one embodiment of the activation of transcription in a pBAD vector via the addition of L-arabinose. Without wishing to be bound by theory, it is believed that L-arabinose binds to the AraC dimer causing the protein to release the $O_2$ site on the DNA and bind to the $I_2$ site. These steps serve to release the DNA loop and enable its transcription. Additionally, the cAMP activator protein (CAP) complex stimulates AraC binding to $I_1$ and $I_2$—a process initiated with IPTG.

3. Targeting Expressed Peptides to Inclusion Bodies

In some cases, cells expressing only a fusion peptide with an affinity tag, a cleavable tag, and the target peptide cannot produce large amounts of fusion peptide. The reasons for low production yields may vary. For example, the fusion peptide may be toxic to the bacteria, thus causing the bacteria to die upon production of certain levels of the fusion peptide. Alternatively, the target peptide may be either poorly expressed or rapidly degraded in the bacterial system. In various scenarios, the target peptide may be modified by the host cell, including modifications such as glycosylation. To remedy some or all of these problems, the desired fusion peptide may be directed to an inclusion body, thereby physically segregating the target peptide from degradative factors in the cell's cytoplasm or, in the case of target peptides that are toxic to the host such as peptide antibiotics, physically segregating the target peptide to avoid toxic effects on the host. Moreover, by physically aggregating the fusion peptide in an inclusion body, the subsequent separation of the fusion peptide from the constituents of the host cell and the media (i.e., cell culture or broth) may be performed more easily or efficiently.

Target peptides may be directed to inclusion bodies by producing the target peptide as part of a fusion peptide where the target peptide is linked either directly or indirectly via intermediary peptides with an inclusion-body directing peptide. In various embodiments, an otherwise identical fusion peptide without an inclusion-body directing peptide has minimal or no tendency to be directed to inclusion bodies in an expression system. Alternatively, an otherwise identical fusion peptide without an inclusion-body directing peptide has some tendency to be directed to inclusion bodies in an expression system, but the number, volume, or weight of inclusion bodies is increased by producing a fusion peptide with an inclusion-body directing peptide. In various embodiments, where the target peptide itself directs the fusion peptide of the invention to inclusion bodies, a separate inclusion-body directing peptide may be excluded.

Any inclusion-body directing peptide may be used according to the methods of the invention. For example, methods have been described which allow α-human atrial natriuretic peptide (α-hANP) to be synthesized in stable form in *E. coli*. Eight copies of the synthetic α-hANP gene were linked in tandem, separated by codons specifying a four amino acid linker with lysine residues flanking the authentic N and C-termini of the 28 amino acid hormone. That sequence was then joined to the 3' end of the fragment containing the lac promoter and the leader sequence coding for the first seven N terminal amino acids of β-galactosidase. The expressed multidomain protein accumulated intracellularly into stable inclusion bodies and was purified by urea extraction of the insoluble cell fraction. The purified protein was cleaved into monomers by digestion with endoproteinase lys C and trimmed to expose the authentic C-terminus by digestion with carboxypeptidase B. See Lennick et al., "High-level expression of α-human atrial natriuretic peptide from multiple joined genes in *Escherichia coli*," Gene, 61:103-112 (1987), incorporated by reference herein.

In various embodiments, directing the target peptide to an inclusion body by producing the target peptide as part of a fusion peptide may lead to higher output of peptide. For example, in various embodiments, the desired fusion peptide is produced in concentrations greater than 100 mg/L. In various embodiments, the desired fusion peptide is produced in concentrations greater than about 200 mg/L, 250 mg/L, 300 mg/L, 350 mg/L, 400 mg/L, 450 mg/L, 500 mg/L, 550 mg/L, 600 mg/L, 650 mg/L, 700 mg/L, 750 mg/L, 800 mg/L, 850 mg/L, 900 mg/L, 950 mg/L, and 1 g/L, all amounts being prefaced by "greater than about." In various embodiments, the output of desired fusion peptide is greater than about 1.5 g/L, greater than about 2 g/L, or greater than about 2.5 g/L. In various embodiments, the output of desired fusion peptide is in the range of from about 500 mg/L to about 2 g/L, or from about 1 g/L to about 2.5 g/L. In one embodiment, the desired fusion peptide is produced in yields equal to or greater than 500 mg/L of media.

In one embodiment, the inclusion-body directing peptide is a ketosteroid isomerase (KSI) or inclusion-body directing functional fragment thereof. In certain embodiments, inclusion-body directing functional fragment has at least 25, at least 30, at least 35, at least 40, at least 45, at least 50, at least 55, at least 60, at least 65, at least 70, at least 75, at least 80, at least 85, at least 90, at least 95, or at least 100 amino acids. Homologs of a ketosteroid isomerase are also encompassed. Such homologs may have at least 25, at least 30, at least 35, at least 40, at least 45, at least 50, at least 55, at least 60, at least 65, at least 70, at least 75, at least 80, at least 85, at least 90, or at least 95 percent sequence identity with the amino acid sequence of a ketosteroid isomerase. In various embodiments, an expression system for a fusion peptide with a functional fragment or homolog of a ketosteroid isomerase will produce at least 25, at least 30, at least 35, at least 40, at least 45, at least 50, at least 55, at least 60, at least 65, at least 70, at least 75, at least 80, at least 85, at least 90, at least 95, or greater than 100 percent of the amount of inclusion bodies produced by an otherwise identical expression system with a fusion peptide containing a complete ketosteroid isomerase peptide sequence.

B. Solid Phase Peptide Synthesis

In one embodiment, the desired fusion peptide is made through solid phase peptide synthesis (SPPS). SPPS involves covalently linking a short peptide to an insoluble polymer providing a structural support for the elongation of the peptide. To achieve elongation of the peptide, the practitioner performs a series of repeated cycles de-protecting the chemically reactive portions of amino acids, linking the de-protected free terminal amine (N) to a single N-protected amino acid, de-protecting the N-terminal amine of the newly added residue, and repeating this process until the desired peptide has been built. Additional measures may be necessary for peptides that are about 50 or more amino acids in length.

In one embodiment, the solid phase peptide synthesis uses Fmoc protecting groups. The Fmoc protecting group utilizes a base labile alpha-amino protecting group. In an alternative embodiment, the solid phase peptide synthesis uses Boc protecting groups. The Boc protecting group is an acid labile alpha-amino protecting group. Each method may involve distinct resin addition, amino acid side-chain protection, and consequent cleavage/deprotection steps. Generally, Fmoc chemistry generates peptides of higher quality and in greater yield than Boc chemistry. Impurities in Boc-synthesized peptides are mostly attributed to cleavage problems, dehydration and t-butylation. Once assembled on the solid support, the peptide is cleaved from the resin using strongly acidic conditions, usually with the application of trifluoracetic acid (TFA). It is then purified using reverse phase high pressure liquid chromatography, or RP-HPLC, a process in which sample is extruded through a densely packed column and the amount of time it takes for different samples to pass through the column (known as a retention time) is recorded. As such, impurities are separated out from the sample based on the principle that smaller peptides pass through the column with shorter retention times and vice versa. Thus, the protein being purified elutes with a characteristic retention time that differs from the rest of the impurities in the sample, thus providing separation of the desired protein.

Solid-phase peptide synthesis generally provides high yields because excess reagents can be used to force reactions to completion. Separation of soluble byproducts is simplified by the attachment of the peptide to the insoluble support throughout the synthesis. Because the synthesis occurs in the same vessel for the entire process, mechanical loss of material is low.

In various embodiments, an inclusion body directing peptide may be excluded. Alternatively, an inclusion body directing peptide may be included to provide beneficial folding properties and/or solubility/aggregating properties.

C. Non-Ribosomal Synthesis

In various embodiments, peptides may be produced by non-ribosomal synthesis. Such peptides include circular peptides and/or depsipeptides.

Nonribosomal peptides are synthesized by one or more nonribosomal peptide synthetase (NRPS) enzymes. These enzymes are independent of messenger RNA. Nonribosomal peptides often have a cyclic and/or branched structure, can contain non-proteinogenic amino acids including D-amino acids, carry modifications like N-methyl and N-formyl groups, or are glycosylated, acylated, halogenated, or hydroxylated. Cyclization of amino acids against the peptide backbone is often performed, resulting in oxazolines and thiazolines; these can be further oxidized or reduced. On occasion, dehydration is performed on serines, resulting in dehydroalanine.

The enzymes of an NRPS are organized in modules that are responsible for the introduction of one additional amino acid. Each module consists of several domains with defined functions, separated by short spacer regions of about 15 amino acids. While not wishing to be bound by theory, it is thought that a typical NRPS module is organized as follows: initiation module, one or more elongation modules, and a termination module. The NRPS genes for a certain peptide are usually organized in one operon in bacteria and in gene clusters in eukaryotes.

In various embodiments, an inclusion body directing peptide may be excluded. Alternatively, an inclusion body directing peptide may be included to provide beneficial folding properties and/or solubility/aggregating properties.

VI. Separation of Fusion Peptide from Formation Media

Following production of the desired fusion peptides, separation from the production media is required. Optionally, following separation, the desired fusion peptide and carrier may be concentrated to remove excess liquid. Numerous methods for separating fusion peptides from their formation media and subsequent handling may be adapted to the invention. Various methods are described in detail herein.

A. Fusion Peptides Targeted to Inclusion Bodies

In various embodiments, the cells used to produce the desired fusion peptides may be lysed to release the fusion peptides. For example, where the desired fusion peptide is aggregated in inclusion bodies, the cell may by lysed, followed by separation of the inclusion bodies from the production media and cellular detritus. Any method of cell lysis may be used according to the invention.

In various embodiments, cells are disrupted using high-power sonication in a lysis buffer. For example, a lysis buffer may be added before lysis containing Tris, sodium chloride, glycerol, and a protease inhibitor. In one embodiment, a lysis buffer containing about 25 mM Tris pH 8.0, about 50 mM NaCl, about 10% glycerol, and the protease inhibitor 1000× PMSF may added before lysis. Insoluble inclusion bodies may be collected using one or more washing steps and centrifugation steps. Wash buffers may include any reagents used for the stabilization and isolation of proteins. For example, in various embodiments, wash buffers are used containing varying concentrations of Tris pH 8.0, NaCl, and Triton X100.

In an embodiment of the invention, targeting the desired fusion peptide to an inclusion body may result in higher initial purity upon lysis of the cell. For example, in one embodiment, lysis of the cell and isolation of inclusion bodies through physical means such as centrifugation may result in an initial purity of greater than about 70%, great than about 75%, greater than about 80%, greater than about 85%, greater than about 90%, or greater than about 95% for the desired fusion peptide.

In some embodiments following cell lysis, inclusion bodies form a pellet and remain in the pellet rather than supernatant until a solubilization step. In various embodiments, the pellet is washed clean of the remaining cellular components, and insoluble inclusion bodies are solubilized in a buffer for further handling. Solubilization buffers may include urea or any other chaotropic agent necessary to solubilize the fusion peptide. Without wishing to be bound by theory, it is believed that the solubilization step involves solubilizing the inclusion bodies in a chaotropic agent which serves to disrupt the peptides by interfering with any stabilizing intra-molecular interactions.

In various embodiments, the solubilization buffer may include urea, guanidinium salts, or organic solvents. For example, a solubilization buffer may contain about 25 mM Tris pH 8.0, about 50 mM, NaCl, about 0.1 mM PMSF, and about 8M urea. In some embodiments, solubilization of inclusion bodies occurs with the addition of 8M urea as the sole chaotropic agent, and other chaotropic agents are excluded. Alternatively, the solubilization buffer may exclude urea or guanidinium salts. For example, in one embodiment, guanidinium salts are excluded to avoid interference with further processing on an ion exchange column. As an additional example, in one embodiment, high urea concentrations such as about 8M urea are excluded to avoid denaturing proteases that may be included in the solubilization buffer.

In various embodiments, a minimal amount of solubilization buffer is used. In the event that excess solubilization buffer is present, the solution may be processed to remove excess solvent prior to further purification.

B. Fusion Peptides not Targeted to Inclusion Bodies

In various embodiments, fusion peptides are not directed to inclusion bodies. In such embodiments, the fusion peptides may remain in the cytosol of the cell, or the fusion peptides according to the invention may be secreted from the cell. Soluble fusion peptides may be isolated by any method, such as centrifugation, gel electrophoresis, pH or ion exchange chromatography, size exclusion chromatography, reversed-phase chromatography, dialysis, osmosis, filtration, and extraction.

VII. Purification by Affinity Chromatography

Following cell lysis and initial isolation and solubilization of fusion peptides according to the invention, the fusion peptides are further purified by affinity chromatography, which is a highly selective process that relies on biologically-relevant interactions between an immobilized stationary phase and the fusion peptide to be purified. In various embodiments, the immobilized stationary phase is a resin or matrix. Without wishing to be bound by theory, it is believed that affinity chromatography functions by selective binding of the desired component from a mixture to the immobilized stationary phase, followed by washing of the stationary phase to remove any unbound material.

Figure 7:
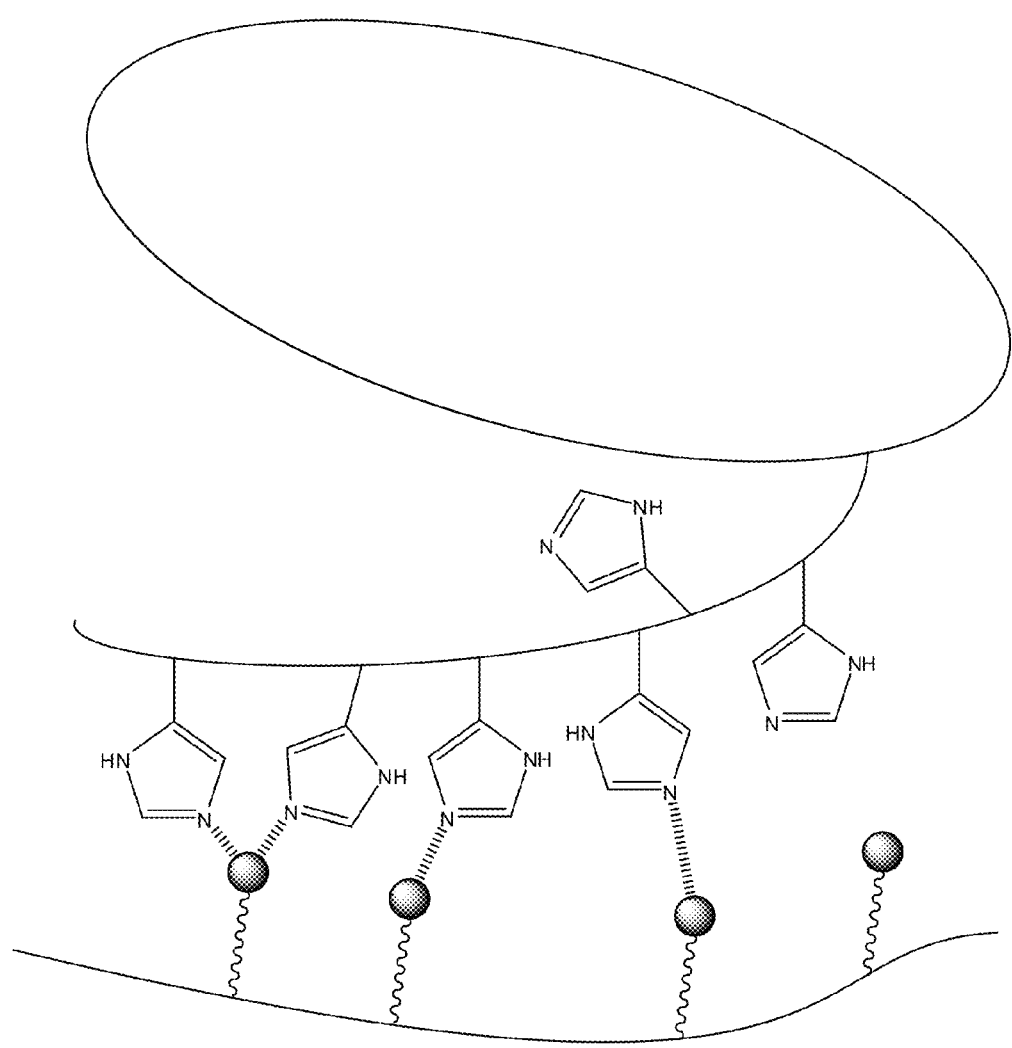
FIG. 7 illustrates one embodiment of an immobilized Ni-NTA resin binding to a 6×His tag on a protein.

According to the invention, a wide variety of affinity chromatography systems may be used. For example, polyhistidine binds with great affinity and specificity to nickel and thus an affinity column of nickel, such as QIAGEN nickel columns, can be used for purification. See, e.g., Ausubel et al., eds., Current Protocols in Molecular Biology 10.11.8 (John Wiley & Sons 1993). Alternatively, Ni-NTA affinity chromatography resin (available from Invitrogen) may be used. FIG. 7 provides a schematic of an example of an immobilized Ni-NTA resin binding to a 6×HisTag on a protein. Metal affinity chromatography has been used as a basis for protein separations. See Arnold, "Metal Affinity Separations: A New Dimension In Protein Processing" Bio/Technology, 9:151-156 (1991). See also Smith et al., "Chelating Peptide-immobilized Metal Ion Affinity Chromatography" J. Biol. Chem., 263:7211-7215 (1988), which describes a specific metal chelating peptide on the $NH_2$ terminus of a protein that can be used to purify that protein using immobilized metal ion affinity chromatography.

According to the invention, the affinity column is equilibrated with buffer which may be the same as used for the solubilization of the fusion peptide. The column is then charged with the solubilized fusion peptide, and buffer is collected as it flows through the column. In various embodiments, the column is washed successively to remove urea and/or other impurities such as endotoxins, polysaccharides, and residual contaminants remaining from the cell expression system.

VIII. Removal of Target Peptide from Affinity Column Via Cleavage

Numerous methods for cleavage of the fusion peptides on the affinity column may be adapted to the invention. In general, the cleavage step occurs by introduction of a cleavage agent which interacts with the cleavage tag of the fusion peptide resulting in cleavage of the fusion peptide and release of the target peptide. Following cleavage, the affinity column may be flushed to elute the target peptide while the portion of the fusion peptide containing the affinity tag remains bound to the affinity column. Following elution of the target peptide, the eluting solution may be condensed to a desired concentration. The target peptide may be further processed and/or packaged for distribution or sale.

Control of the cleavage reaction may occur through chemical selectivity. For example, the cleavage tag may include a unique chemical moiety which is absent from the remainder of the fusion peptide such that the cleavage agent selectively interacts with the unique chemical moiety of the cleavage tag.

In various embodiments, control of the cleavage reaction occurs through a unique local environment. For example, the cleavage tag may include a chemical moiety that is present elsewhere in the fusion peptide, but the local environment differs resulting in a selective cleavage reaction at the cleavage tag. For example, in various embodiments, the cleavage tag includes a tryptophan and a charged amino acid side chain within five amino acids of the tryptophan. In various embodiments, the charged amino acid is on the amino terminus of the tryptophan amino acid.

In various embodiments, control of the cleavage reaction may occur through secondary or tertiary structure of the fusion peptide. For example, in various embodiments, where identical moieties are present in the cleavage tag and elsewhere in the fusion peptide, the other portions of the fusion peptide may fold in secondary or tertiary structure such as alpha-helices, beta-sheets, and the like, to physically protect the susceptible moiety, resulting in selective cleavage at the cleavage tag.

In various embodiments, minor or even major differences in selectivity of the cleavage reaction for the cleavage tag over other locations in the fusion peptide may be amplified by controlling the kinetics of the cleavage reaction. For example, in various embodiments, the concentration of cleavage agent is controlled by adjusting the flow rate of eluting solvent containing cleavage agent. In various embodiments, the concentration of cleavage agent is maintained at a low level to amplify differences in selectivity. In various embodiments, the reservoir for receiving the eluting solvent contains a quenching agent to stop further cleavage of target peptide that has been released from the column.

Moreover, various methods for removal of peptides from affinity columns may be excluded. For example, methods according to the invention may specifically exclude the step of washing an affinity column with a solution of a compound with competing affinity in the absence of a cleavage reaction. In one embodiment, the step of washing an affinity column with a solution of imidazole as a displacing agent to assist in removing a fusion peptide from an affinity column is specifically excluded.

In various embodiments, multiple cleavages are envisioned. For example, insulin is known to be produced from a proinsulin precursor requiring two cleavage events. Both cleavage events are required in order for the mature insulin to be properly folded. Accordingly, in various embodiments, the process according to the invention may include two cleavage tags. Preferably, when more than one cleavage tag is present, the distinct cleavage tags are orthogonal, or able to be cleaved with specificity by different cleavage agents. For example, in one embodiment, one cleavage tag is a methionine amino acid while the other cleavage tag is a tryptophan amino acid.

In various embodiments, the cleavage agent is selected from the group consisting of NBS, NCS, cyanogen bromide, $Pd(H_2O)_4$, 2-ortho iodobenzoic acid, DMSO/sulfuric acid, or a proteolytic enzyme. Various methods and cleavage agents are described in detail herein.

A. NBS Cleavage

Figure 9:
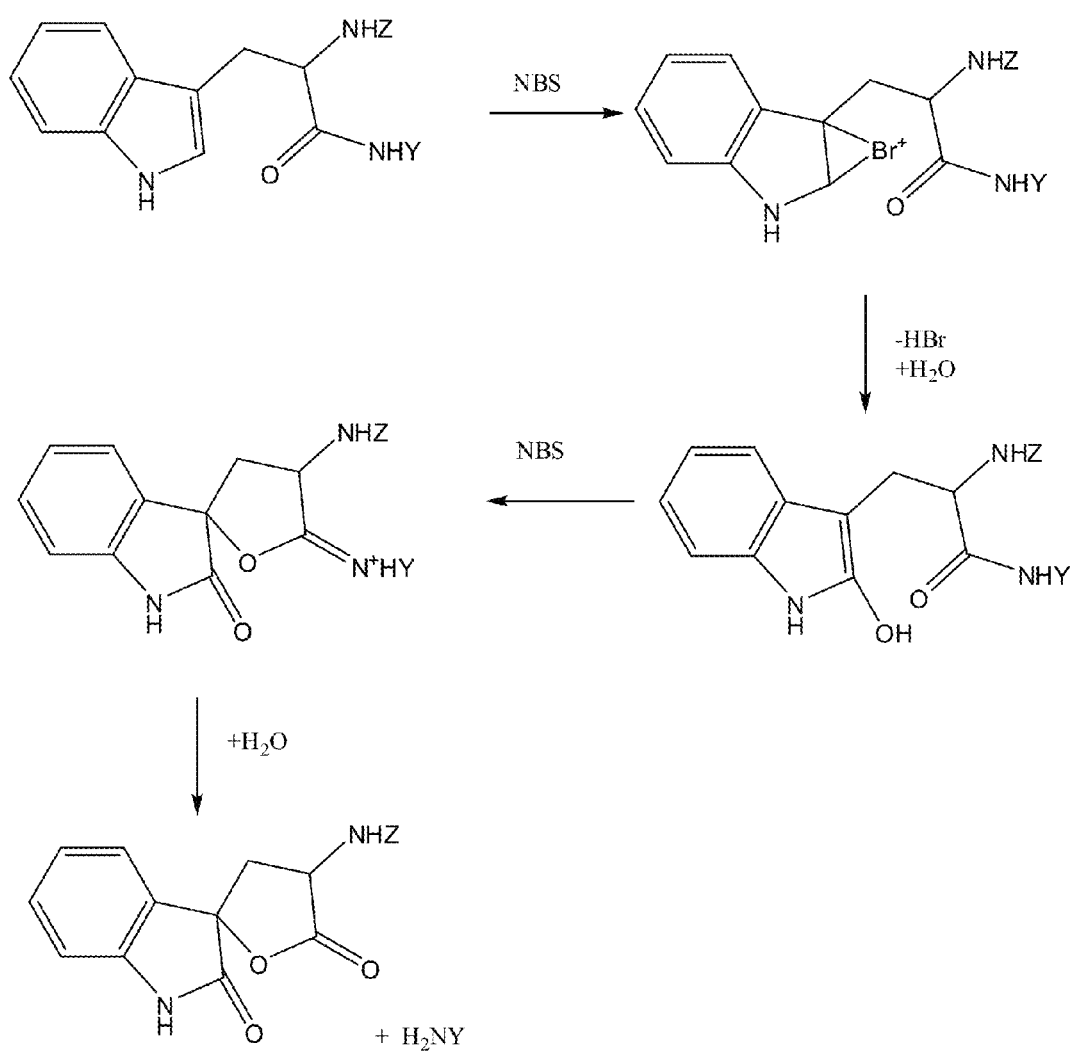
FIG. 9 illustrates one possible mechanism for the selective cleavage of tryptophan peptide bonds with NBS (N-bromosuccinimide). According to the mechanism, the active bromide ion halogenates the indole ring of the tryptophan residue followed by a spontaneous dehalogenation through a series of hydrolysis reactions. These reactions lead to the formation of an oxindole derivative which promotes the cleavage reaction.

In one embodiment, the cleavage reaction according to the invention involves the use of a mild brominating agent N¬ bromosuccinimde (NBS) to selectively cleave a tryptophanyl peptide bond at the amino terminus of the target peptide. Without wishing to be bound by theory, it is believed that in aqueous and acidic conditions, NBS oxidizes the exposed indole ring of the tryptophan side chain, thus initiating a chemical transformation that results in cleavage of the peptide bond at this site. FIG. 9 illustrates one possible mechanism for the selective cleavage of tryptophan peptide bonds with N-bromosuccinimde According to the mechanism, the active bromide ion halogenates the indole ring of the tryptophan residue followed by a spontaneous dehalogenation through a series of hydrolysis reactions. These reactions lead to the formation of an oxindole derivative which promotes the cleavage reaction.

B. NCS Cleavage

In one embodiment, the cleavage reaction according to the invention involves the use of a mild oxidizing agent N¬ chlorosuccinimde (NCS) to selectively cleave a tryptophanyl peptide bond at the amino terminus of the target peptide. Without wishing to be bound by theory, it is believed that in aqueous and acidic conditions, NCS oxidizes the exposed indole ring of the tryptophan side chain, thus initiating a chemical transformation that results in cleavage of the peptide bond at this site.

C. Enzymatic Cleavage

In various embodiments, enzymes may be employed to cleave the fusion protein. For example, Protease use is diverse yet selective as there are many proteases that recognize specific amino acid sequences. In various embodiments, the active site of a serine or threonine protease will bind to either serine or threonine, respectively, and intitiate catalytic mechanisms that result in proteolysis. Additional enzymes include collagenase, enterokinase factor $X_A$, thrombin, trypsin, clostripain and alasubtilisin. See Uhlen and Moks, Meths. in Enz., 185:129-143 (1990) and Emtage, "Biotechnology & Protein Production" in Delivery Systems for Peptide Drugs, pp. 23-33 (1986).

D. Additional Chemical Agents

In various embodiments, the cleavage agent is a chemical agent such as cyanogen bromide, palladium (II) aqua complex (such as $Pd(H_2O)_4$), formic acid, and hydroxylamine. For example, cyanogen bromide may be used to selectively cleave a fusion peptide at a methionine amino acid at the amino terminus of the target peptide.

IX. Downstream Processing

In various embodiments, target peptides produced according to the process of the invention may be further modified. For example, in various embodiments, the C-terminus of the target peptide is connected to alpha-hydroxyglycine. At the desired time, the target peptide, either as the isolated target peptide or as part of the fusion peptide, is exposed to acid catalysis to yield glycolic acid and a carboxamide group at the carboxy terminus of the target peptide. A carboxamide group at the carboxy terminus is present in a variety of neuropeptides, and is thought to increase the half-life of various peptides in vivo.

In various embodiments, target peptides produced according to the invention may be further modified to alter in vivo activity. For example, in various embodiments, a polyethylene glycol (PEG) group may be added to a target peptide.

X. Peptide Marketing

Methods according to the invention are also directed to marketing the target peptides produced according to the methods of the invention. For example, in one embodiment, the invention is directed a method of evaluating the commercial market for a target peptide. Such methods may include producing a target peptide as described herein, making sample amounts of the target peptide available for no cost or for minimal cost, and measuring the number of requests for the target peptide over a period of time. Advantages of making a target peptide available in this manner may include an improved calculation of the future supplies needed and/or future demand by paying customers. Alternatively, providing a target peptide at no cost or minimal cost initially may induce interest in the target peptide and the discovery of favorable characteristics for the peptide that spur future sales. Minimal cost may include a price that is approximately the cost of production with essentially no profit involved. In various embodiments, the minimal cost may be about 10%, about 20%, about 30%, about 40%, about 50%, about 60%, or about 70% of the price of a competitor's product.

INCORPORATION BY REFERENCE

All publications, patents, and patent applications mentioned in this specification are herein incorporated by reference to the same extent as if each individual publication, patent, or patent application was specifically and individually indicated to be incorporated by reference.

EXAMPLES

The examples herein provide some non-limiting examples according to the invention. The following examples include both actual examples and prophetic examples.

Example 1

Cells were induced to initiate the synthesis of KSI-Abeta (1-42) with 1 mM IPTG (Invitrogen) and 0.2% L-arabinose (Calbiotech) as follows. Plated cells are incubated overnight at 37° C. and then one colony from this plate was grown up overnight in a starter culture of 8 mL of Luria broth+ampicillin. The following morning, the starter culture was inoculated into 1 L of Luria broth+ampicillin and grown to an optical density (OD) of 0.5. At this point, the cells were induced with 1 mM IPTG (Invitrogen) and 0.2% L-arabinose (Calbiotech) to initiate the synthesis of KSI-Abeta (1-42).

Figure 3:
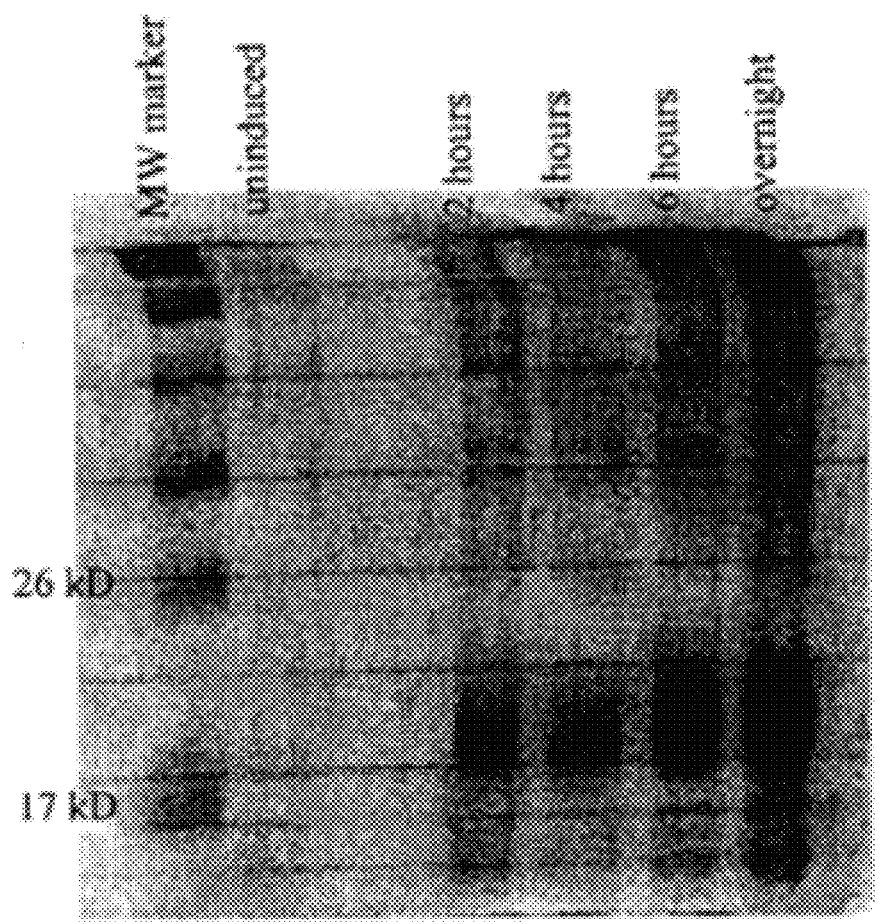
FIG. 3 shows exemplary data for gel electrophoresis of samples taken from a cell culture prior to induction and then 2, 4, 6, and 16 hours post-induction. Optimal fusion protein synthesis occurs when the culture is induced and grown overnight.

To optimize the amount of KSI-Abeta (1-42) production in the bacteria, samples of the 1 L inoculation were taken prior to inducing the bacteria, and then 2, 4, 6, and 16 hours (overnight growth) after induction. A 12% acrylamide gel was used to analyze the samples since the fusion protein weighs approximately 21 kD. FIG. 3 shows exemplary data for gel electrophoresis of samples taken from a cell culture prior to induction and then 2, 6, and 16 hours post-induction. Optimal fusion protein synthesis occurred when the culture was induced and grown overnight.

Eight hours after induction, the cells were re-induced with the same concentrations of IPTG and L-arabinose as well as 100 mg of ampicillin as to prevent the growth of any new strains of *E. coli*.

Example 1A

The construct was re-designed to place a His-tag upstream from the KSI sequence rather than downstream.

Example 2

Following induction of KSI-Abeta (1-42) production in *E. coli*, lysis buffer containing 25 mM Tris pH 8.0, 50 mM NaCl, 10% glycerol, and the protease inhibitor 1000×PMSF was added before lysis. Insoluble inclusion bodies were collected using washing and centrifugation. Three different wash buffers were used containing varying concentrations of Tris pH 8.0, NaCl, and Triton X100. Once washed clean of the remaining cellular components, the insoluble inclusion bodies were solubilized in a buffer containing 25 mM Tris pH 8.0, 50 mM, NaCl, 0.1 mM PMSF, and 8M urea. The 8M urea served as a chaotropic agent necessary in solubilizing protein.

Figure 6:
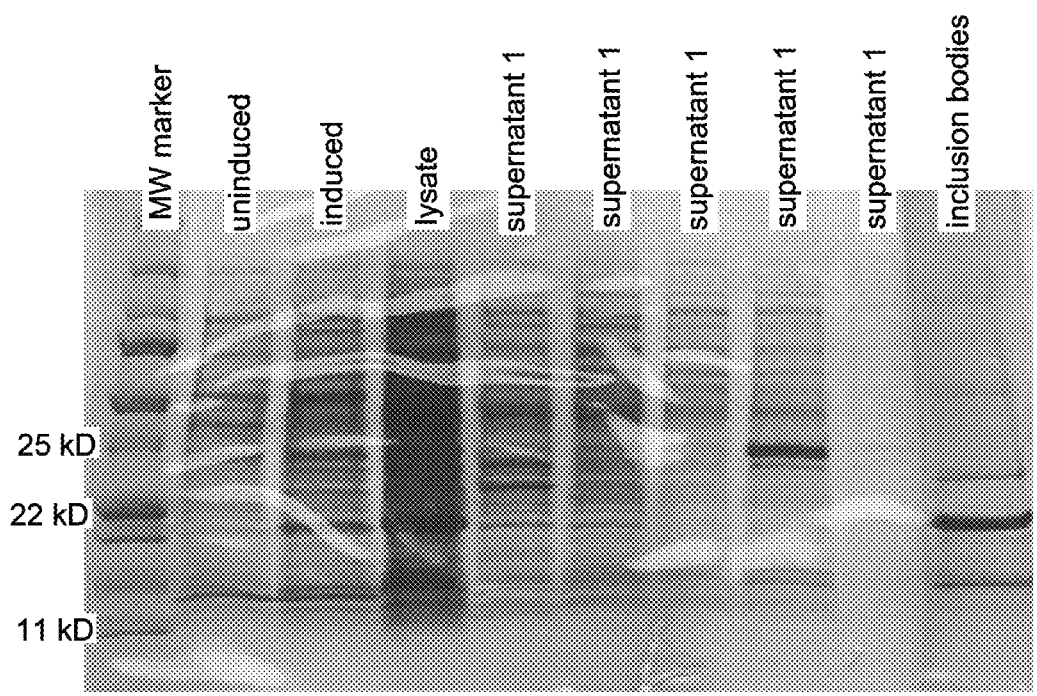
FIG. 6 shows exemplary data for the stages of inclusion body preparation by gel electrophoresis of cells lysed with high-power sonication. The lysed material was washed with a series of buffers containing different concentrations of Tris, NaCl, PMSF, Triton-X100, and urea, and the supernatant was collected. The disappearance of the 21 kD band during successive steps and reappearance of the 21 kD band upon solubilizing the inclusion bodies (lane 10) indicates that the inclusion bodies were properly prepared.

A 12% acrylamide gel was run on both uninduced and induced bacteria, the cell lysate produced from high output sonication, and the supernatant from each washing step during the inclusion body preparation. The gel was stained with Coomassie Blue reagent. The appearance of a 21 kD in the induced sample provides evidence for inclusion body synthesis resulting from induction. FIG. 6 presents exemplary data showing the stages of inclusion body preparation by gel electrophoresis of cells lysed with high-power sonication and washed with a series of buffers containing different concentrations of Tris, NaCl, PMSF, Triton-X100, and urea. The disappearance of the 21 kD band during successive steps and reappearance of the 21 kD band upon solubilizing the inclusion bodies (lane 10) indicated that the inclusion bodies were properly prepared. Accordingly, the lane containing the cell lysate was almost entirely blue because as the cells are ruptured, relatively large quantities of various proteins were extracted. As the lysate was washed repeatedly of impurities, the lanes became clearer.

Example 3

Figure 10:
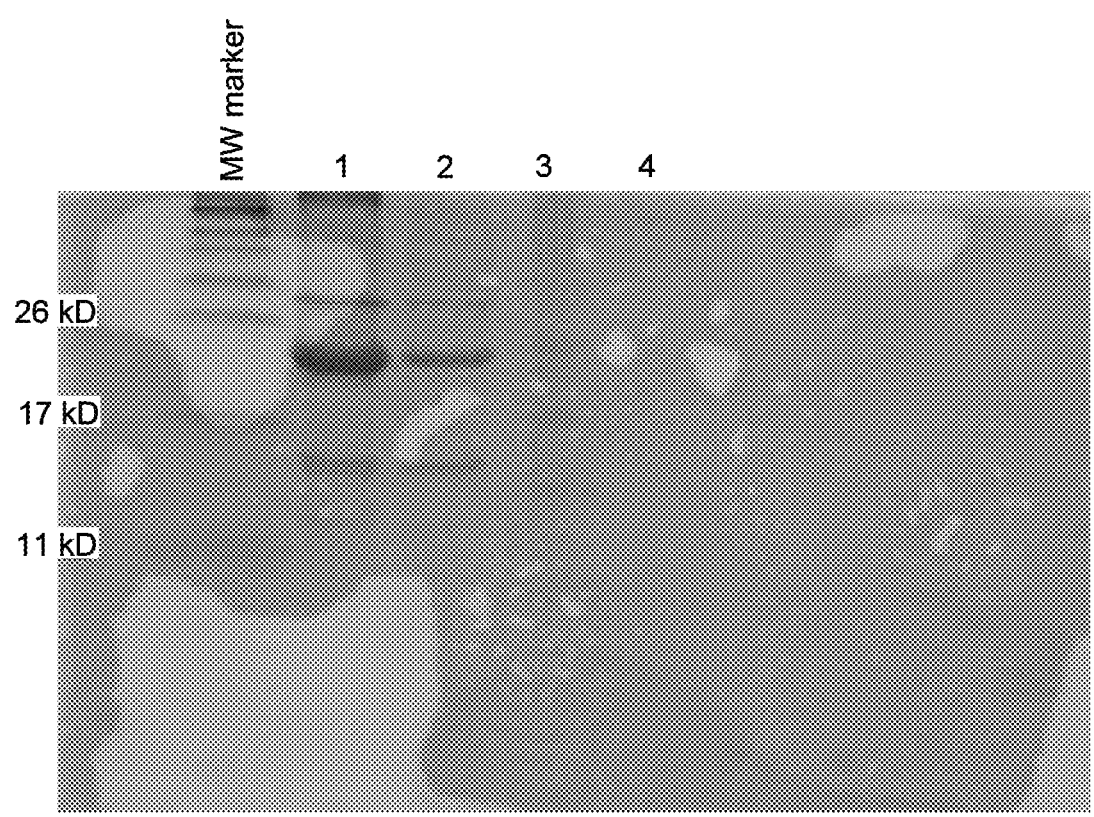
FIG. 10 presents exemplary data for gel electrophoresis of nine different NBS cleavage reactions. The reactions were performed and the samples were run on an 18% acrylamide gel and silver stained. Lane (1) stock inclusion bodies; lane (2) 0×NCS for 0 min; lane (3) 1×NBS for 30 min; lane (4) 1×NBS for 60 min; lane (5) 3×NBS for 0 min; lane (6) 3×NBS for 30 min; lane (7) 3×NBS for 60 min; lane (8) 6×NBS for 0 min; lane (9) 6×NBS for 30 min; lane (10) 6×NBS for 60 min.

The concentration of protein in solubilized inclusion bodies was determined via a Bradford Assay. A series of NBS cleavage reactions was run to determine the optimal conditions for tryptophanyl peptide bond cleavage. Three concentrations of NBS purchased from TCI America (equimolar, 3×, and 6×) were allowed to react with KSI-Abeta (1-42) for varying amounts of time (0, 15, and 30 minutes) before being quenched with excess N-acetylmethionine (Acros). Since the amyloid beta cleavage product weighed only 5 kD, a higher percentage acrylamide gel (18%) was used to determine the success of the NBS cleavage in solution. The gel indicated that optimal cleavage occurred when 6×NBS was reacted with KSI-Abeta (1-42) at room temperature from 0 to 30 minutes. FIG. 10 presents exemplary data for gel electrophoresis of nine different NBS cleavage reactions. The samples were run on an 18% acrylamide gel and silver stained. Lane (1) stock inclusion bodies; lane (2) OX NCS for 0 min; lane (3) 1×NBS for 30 min; lane (4) 1×NBS for 60 min; lane (5) 3×NBS for 0 min; lane (6) 3×NBS for 30 min; lane (7) 3×NBS for 60 min; lane (8) 6×NBS for 0 min; lane (9) 6×NBS for 30 min; lane (10) 6×NBS for 60 min.

Example 4

Ni-NTA Affinity Chomatography resin purchased from Invitrogen was equilibrated with the same solubilization buffer as in the inclusion body preparation. Next, the resin was charged with the solubilized inclusion bodies and the flow through was collected. The column was then washed with five column volumes of 50% EtOH to remove urea and flow through. Afterwards, 3×NBS was loaded and the column was placed on a rocker for 30 minutes. At this time, the reaction was quenched with excess N-acetylmethionine and the flow through was collected. The column was then washed with 300 mM imidazole to discharge the remaining fusion protein and the flow through was collected.

Figure 8:
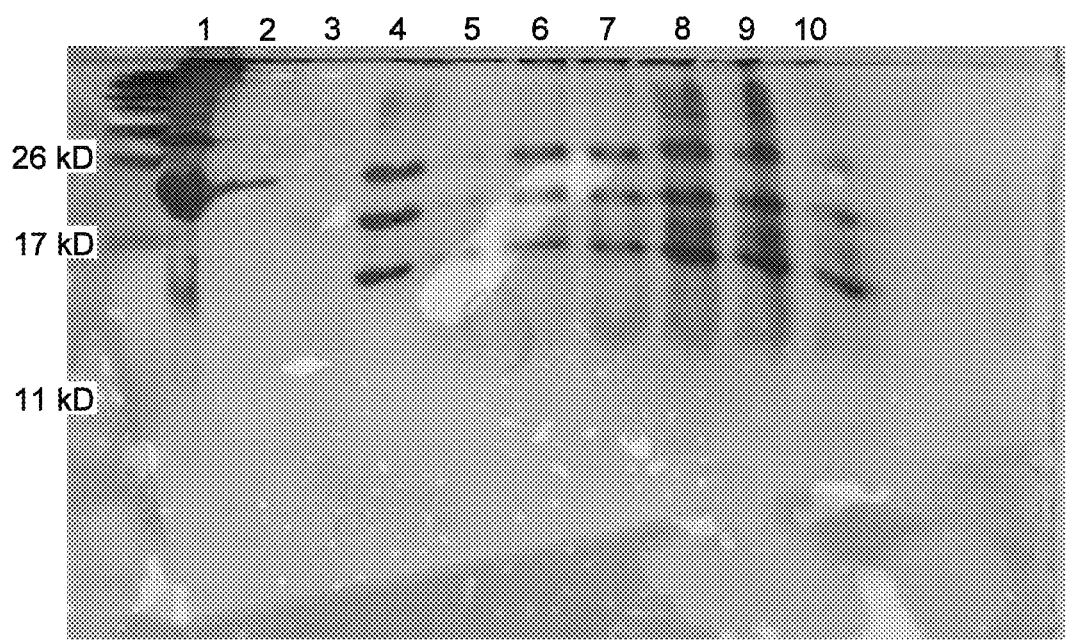
FIG. 8 presents exemplary data showing gel electrophoresis following Ni-NTA affinity chromatography. Inclusion bodies were loaded onto an equilibrated Ni-NTA column and washed with the same buffer, collecting the flow-through (lane 1). The column was then washed with 50% EtOH as to equilibrate it with the cleavage solution buffer (lane 2). On-column cleavage was performed with 3×NBS for 30 minutes at room temperature and the flow through was collected (lane 3). The column was washed with 300 mM imidazole to wash off all remaining fusion protein and the flow-through was collected (lane 4).

SDS-PAGE analysis indicated that a very small amount of inclusion bodies adhere to the Ni-NTA column as evidenced by the appearance of a large 21 kD band in the first wash. FIG. 8 presents exemplary data for gel electrophoresis following Ni-NTA affinity chromatography as follows. Inclusion bodies were loaded onto an equilibrated Ni-NTA column and washed with the same buffer, collecting the flow-through (lane 1). The column was then washed with 50% EtOH as to equilibrate it with the cleavage solution buffer (lane 2). On-column cleavage was performed with 3×NBS for 30 minutes at room temperature and the flow through was collected (lane 3). The column was washed with 300 mM imidazole to wash off all remaining fusion protein and the flow-through was collected (lane 4). A narrower band appeared after the second wash in EtOH to equilibrate the column for the on-column cleavage. A very minor amount of cleavage did occur on the remaining KSI-Abeta (1-42). Incubating the inclusion bodies overnight on a rocker did not improve on-column cleavage, although it did improve the initial binding of KSI-Abeta (1-42) to the column.

Example 5

Figure 11:
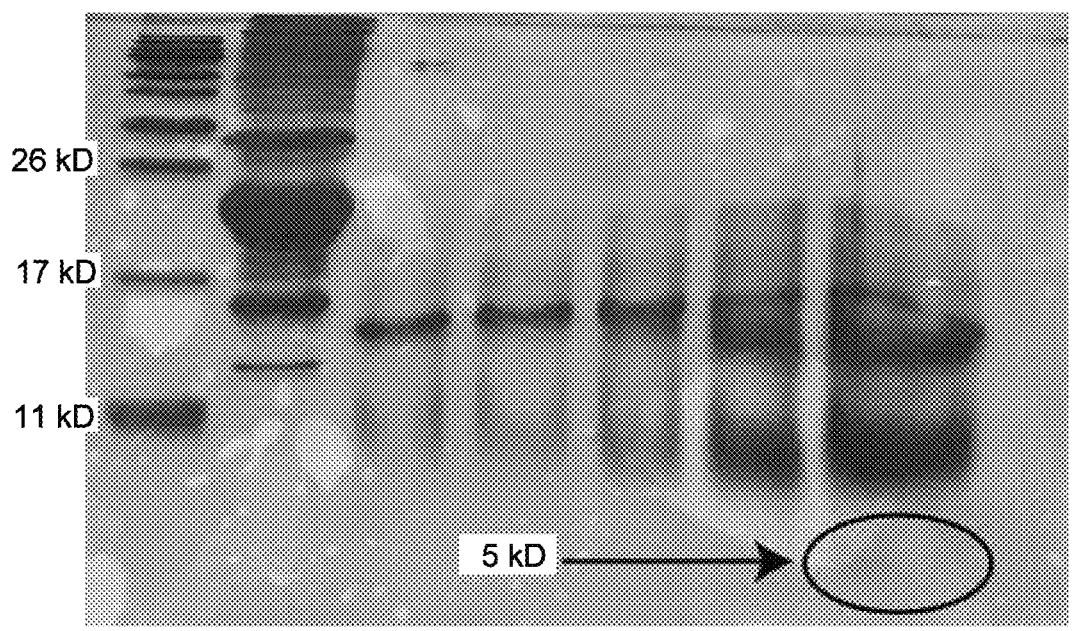
FIG. 11 presents exemplary data showing gel electrophoresis of inclusion bodies that were reacted with 3×NBS for 30 min and then quenched with N-acetylmethionine. The same sample was loaded in increasing quantities from 10 to 25 µl to show appearance of 5 kD cleavage product.

SDS-PAGE analysis on the NBS solution cleavage indicated that the cleavage was successful in solution. FIG. 11 presents exemplary data showing gel electrophoresis of inclusion bodies that were reacted with 3×NBS for 30 min and then quenched with N-acetylmethionine. The same sample was loaded in increasing quantities (from 10 to 25 µl) to show appearance of 5 kD cleavage product.

Because optimal cleavage rates range from 35-45 percent, only a small amount of KSI-Abeta (1-42) was produced. Since the gel contained a small amount of diluted sample, the assay did not detect the 5 kD cleavage product with Coomassie Blue staining. Therefore, visualizing the cleavage product required overloading the sample and overdeveloping the silver stain. See, FIG. 11, faint appearance of the 5 kD band in the two rightmost lanes.

Example 6

The manufacturing cost analysis of direct materials used indicated that the cost to synthesize beta-Amyloid (1-42) through a combination of recombinant expression, chemical manipulation, and purification is drastically lower than the prices charged by other manufacturers (noting that a large makeup of their prices contains overheads, operating costs, labor costs, etc.). Assuming an average yield of inclusion bodies for a 1 liter culture is approximately 5 grams per liter and a 50% NBS cleavage rate, as well as considering product lost during purification, an estimated $0.11 in materials is all that is necessary to synthesize 1 mg of beta-Amyloid (1-42). Even after factoring all of the other manufacturing costs such as facilities, equipment, and labor into the price, the synthesis of beta-Amyloid (1-42) using this method could cost much less to the consumer. See FIG. 12.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

---

What is claimed is:

1. A method for producing a target peptide, the method comprising:
   a) expressing a heterologous fusion peptide in a genetically modified cell, the heterologous fusion peptide comprising an affinity tag, a cleavable tag, and the target peptide, wherein the cleavable tag is tryptophan (Trp), and wherein the affinity tag or the cleavable tag is heterologous to the target peptide;
   b) solubilizing the heterologous fusion peptide;
   c) binding said heterologous fusion peptide to an affinity material via the affinity tag;
   d) cleaving said heterologous fusion peptide with N-chlorosuccinimide while bound to the affinity material to release the target peptide, thereby producing the target peptide; and
   e) removing the target peptide from the affinity material.

2. The method of claim 1, wherein said target peptide is selected from the group consisting of amyloid beta, calcitonin, enfuvirtide, epoetin, epoetin delta, erythropoietin, exenatide, factor VIII, factor X, glucocerebrosidase, glucagon-like peptide-1 (GLP-1), granulocyte-colony stimulating factor (G-CSF), human growth hormone (hGH), insulin, insulin A, insulin B, insulin-like growth factor 1 (IGF-1), interferon, liraglutide, somatostatin, teriparatide, and tissue plasminogen activator (TPA).

3. The method of claim 1, wherein said step of expressing a heterologous fusion peptide in a genetically modified cell is performed in a bacterial expression system.

4. The method of claim 3, wherein said bacterial expression system is an *Escherichia coli* expression system.

5. The method of claim 3, wherein said fusion peptide further comprises an inclusion-body directing peptide.

6. The method of claim 5, wherein prior to binding said heterologous fusion peptide to the affinity material, said method further comprises removal of inclusion bodies containing the fusion peptide from the bacterial expression system and solubilization of the fusion peptide in the inclusion bodies.

7. The method of claim 5, wherein said inclusion-body directing peptide is selected from the group consisting of a ketosteroid isomerase, and a BRCA2 peptide.

8. The method of claim 1, wherein subsequent to binding said heterologous fusion peptide to the affinity material, said method further comprises washing the affinity material to remove unbound material.

9. The method of claim 1, wherein said affinity tag is selected from the group consisting of poly-histidine, poly-lysine, poly-aspartic acid, and poly-glutamic acid.

10. The method of claim 1, wherein the fusion peptide is secreted from the cell after expressing the heterologous fusion peptide.

11. The method of claim 1, further comprising lysing the cell after expressing the heterologous fusion peptide.

12. The method of claim 1, wherein the target peptide that is produced is greater than 99% pure.

13. A method for producing a target peptide, the method comprising:

a) expressing a heterologous fusion peptide in a genetically modified cell, the heterologous fusion peptide comprising an affinity tag, a cleavable tag, and the target peptide, wherein the cleavable tag is Trp, and wherein the affinity tag or the cleavable tag is heterologous to the target peptide;
b) solubilizing the heterologous fusion peptide;
c) binding said heterologous fusion peptide to an affinity material via the affinity tag; and
d) cleaving said heterologous fusion peptide with N-chlorosuccinimide while bound to the affinity material to release the target peptide, thereby producing the target peptide.

14. A method for producing a target peptide, the method comprising:
a) expressing a heterologous fusion peptide in a genetically modified cell, the heterologous fusion peptide comprising an affinity tag, a cleavable tag, and the target peptide, wherein the cleavable tag is Trp, and wherein the affinity tag or the cleavable tag is heterologous to the target peptide;
b) solubilizing the heterologous fusion peptide;
c) binding said heterologous fusion peptide to an affinity material via the affinity tag; and
d) cleaving said heterologous fusion peptide with DMSO/sulfuric acid while bound to the affinity material to release the target peptide, thereby producing the target peptide.

15. The method of claim 14 wherein said target peptide is selected from the group consisting of amyloid beta, calcitonin, enfuvirtide, epoetin, epoetin delta, erythropoietin, exenatide, factor VIII, factor X, glucocerebrosidase, glucagon-like peptide-1 (GLP-1), granulocyte-colony stimulating factor (G-CSF), human growth hormone (hGH), insulin, insulin A, insulin B, insulin-like growth factor 1 (IGF-1), interferon, liraglutide, somatostatin, teriparatide, and tissue plasminogen activator (TPA).

16. The method of claim 14, wherein said step of producing a heterologous fusion peptide is performed in a bacterial expression system.

17. The method of claim 16, wherein said bacterial expression system is an *Escherichia coli* expression system.

18. The method of claim 16, wherein said heterologous fusion peptide further comprises an inclusion-body directing peptide.

19. The method of claim 18, wherein prior to binding said heterologous fusion peptide to an affinity material, said method further comprises removal of inclusion bodies containing the heterologous fusion peptide from the bacterial expression system and solubilization of the heterologous fusion peptide in the inclusion bodies.

20. The method of claim 18, wherein said inclusion-body directing peptide is selected from the group consisting of a ketosteroid isomerase, and a BRCA2 peptide.

21. The method of claim 14, wherein subsequent to binding said heterologous fusion peptide to the affinity material, said method further comprises washing the affinity material to remove unbound material.

22. The method of claim 14, wherein said affinity tag is selected from the group consisting of poly-histidine, poly-lysine, poly-aspartic acid, or poly-glutamic acid.

23. The method of claim 14, wherein the fusion peptide is secreted from the cell after expressing the heterologous fusion peptide.

24. The method of claim 14, further comprising lysing the cell after expressing the heterologous fusion peptide.

25. The method of claim 14, wherein the target peptide that is produced is greater than 99% pure.

* * * * *

SEQUENCE LISTING

```
<160> NUMBER OF SEQ ID NOS: 13

<210> SEQ ID NO 1
<211> LENGTH: 132
<212> TYPE: PRT
<213> ORGANISM: Comamonas testosteroni
<220> FEATURE:
<223> OTHER INFORMATION: strain CNB-2

<400> SEQUENCE: 1

Met Ser Lys Gln Glu Ser Gln Pro Asp Val Gln Phe Leu Ala Arg Phe
1               5                   10                  15

Ser Asp Ala Trp Asn Arg His Asp Ile Asp Ala Leu Met Asp Phe Met
                20                  25                  30

Ala Asp Glu Cys Glu Phe His Ala Val Ala Gly Pro Asp Leu Met Gly
            35                  40                  45

Arg Ser Phe Val Gly Arg Glu Ala Val Arg Glu Gly Phe Gln Leu Ala
        50                  55                  60

Trp Gln Ala Phe Pro Asp Ala Ala Trp Val Asp Gly Glu His Phe Val
65                  70                  75                  80

Gln Gly Thr Arg Gly Val Ser Glu Ser Thr Phe Lys Gly Thr Lys Ala
                85                  90                  95
```

```
Asp Gly Leu Arg Val Glu Ala Arg Met Val Asp Val Phe Thr Phe Arg
            100                 105                 110

Asp Gly Lys Ile Ala Val Lys Asn Ala Tyr Arg Lys Asp Arg Pro Pro
        115                 120                 125

Val Ala Ile Ser
    130

<210> SEQ ID NO 2
<211> LENGTH: 148
<212> TYPE: PRT
<213> ORGANISM: Legionella pneumophila
<220> FEATURE:
<223> OTHER INFORMATION: strain Corby; ketosteroid isomerase

<400> SEQUENCE: 2

Met Lys Ser Ile Ala Asn Lys Glu Asn Glu Val Ala Ile Ile His Lys
1               5                   10                  15

Leu Ile Glu Glu Tyr Ala Asn Ala Ala Arg Asp Lys Asp Ile Asp Lys
            20                  25                  30

Ile Met Ser His Tyr Ala Pro Asp Ile Arg Ser Phe Asp Ala Tyr Ser
        35                  40                  45

Gln Leu Gln Phe Lys Gly Ala Asp Tyr Arg Lys His Trp Gln Thr
    50                  55                  60

Cys Leu Ser Phe Cys Pro Gly Pro Ser Val Phe Glu Val His Gln Leu
65                  70                  75                  80

Glu Thr Ile Val Asp Asn Asn Leu Ala Val Ser Tyr Tyr Leu Thr Tyr
                85                  90                  95

Cys Gly Gly Thr Asn Glu Lys Gly Glu Thr Gln Gly Gly Trp Met Arg
            100                 105                 110

Gly Thr Met Val His Cys Lys Met Asn Gly Lys Trp Lys Ile Met His
        115                 120                 125

Glu His Tyr Ser Ile Pro Phe Asp Met Lys Thr Gly Asn Thr Leu Phe
    130                 135                 140

Asp Leu Lys Pro
145

<210> SEQ ID NO 3
<211> LENGTH: 153
<212> TYPE: PRT
<213> ORGANISM: Pseudomonas stutzeri
<220> FEATURE:
<223> OTHER INFORMATION: strain A1501; ketosteroid isomerase

<400> SEQUENCE: 3

Met Asn Asn Thr Thr Arg Gln Asp Glu Thr Ala Ile Arg Gln Leu His
1               5                   10                  15

Asp Ala Phe Glu Gln Ala Ile Gly Ala Lys Asp Leu Asp Arg Ile Met
            20                  25                  30

Ala Gln Tyr Ala Pro Asp Val Val Ala Phe Asp Ala Val Gly Ala Leu
        35                  40                  45

Gln Phe Lys Gly Val Ala Glu Tyr Arg Ala His Trp Gln Arg Cys Phe
    50                  55                  60

Glu Phe Cys Gln Gly Gly Phe Phe Glu Thr His Glu Leu His Val
65                  70                  75                  80

Asp Val Gly Gly Glu Leu Ala Cys Ser Arg Met Leu Thr His Cys Gly
                85                  90                  95

Gly Pro Asn Ala Glu Gly Glu Met Gln Thr Ala Trp Met Arg Gly Thr
```

```
                    100                 105                 110
Arg Val Trp Ala Arg Arg Asp Gly Glu Trp Lys Val Ile His Glu His
            115                 120                 125

Phe Ser Met Pro Phe Asp Met Glu Thr Gly Gln Val Cys Met Ser Ser
        130                 135                 140

Thr Pro Ser Ala Thr Gln Gln Val Gly
145                 150

<210> SEQ ID NO 4
<211> LENGTH: 124
<212> TYPE: PRT
<213> ORGANISM: Pseudomonas testosteroni
<220> FEATURE:
<223> OTHER INFORMATION: delta 5-3-ketosteroid isomerase

<400> SEQUENCE: 4

His Thr Pro Glu His Ile Thr Ala Val Val Gln Arg Phe Val Ala Ala
1               5                   10                  15

Leu Asn Ala Gly Asp Leu Asp Gly Ile Val Ala Leu Phe Ala Asp Asp
            20                  25                  30

Ala Thr Val Glu Asp Pro Val Gly Ser Glu Pro Arg Ser Gly Thr Ala
        35                  40                  45

Ala Ile Arg Glu Phe Tyr Ala Asn Ser Leu Lys Leu Pro Leu Ala Val
    50                  55                  60

Glu Leu Thr Gln Glu Val Arg Ala Val Ala Asn Glu Ala Ala Phe Ala
65                  70                  75                  80

Phe Thr Val Ser Phe Glu Tyr Gln Gly Arg Lys Thr Val Val Ala Pro
                85                  90                  95

Ile Asp His Phe Arg Phe Asn Gly Ala Gly Lys Val Val Ser Ile Arg
            100                 105                 110

Ala Leu Phe Gly Glu Lys Asn Ile His Ala Cys Gln
        115                 120

<210> SEQ ID NO 5
<211> LENGTH: 378
<212> TYPE: DNA
<213> ORGANISM: Pseudomonas testosteroni
<220> FEATURE:
<223> OTHER INFORMATION: ketosteroid isomerase (ksi) gene

<400> SEQUENCE: 5 catacoccag aacacatcac cgccgtggta cagcgctttg tggctgcgct caatgccggc      60
gatctggacg gcatcgtcgc gctgtttgcc gatgacgcca cggtggaaga ccccgtgggt    120
tccgagccca ggtccggtac ggctgcgatt cgtgagtttt acgccaactc gctcaaactg    180
cctttggcgg tggagctgac gcaggaggta cgcgcggtcg ccaacgaagc ggccttcgct    240
ttcaccgtca gcttcgagta tcagggccgc aagaccgtag ttgcgcccat cgatcacttt    300
cgcttcaatg cgccggcaa ggtggtgagc atccgcgcct gtttggcga agaatatt    360 cacgcatgcc agctcgag                                                  378

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 6
```

```
His His His His His His
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(10)
<223> OTHER INFORMATION: This sequence may encompass 5-10 repeating
      'Lys' residues

<400> SEQUENCE: 7

Lys Lys Lys Lys Lys Lys Lys Lys Lys Lys
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(10)
<223> OTHER INFORMATION: This sequence may encompass 5-10 repeating
      'His' residues

<400> SEQUENCE: 8

His His His His His His His His His His
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(10)
<223> OTHER INFORMATION: This sequence may encompass 5-10 repeating
      'Glu' residues

<400> SEQUENCE: 9

Glu Glu Glu Glu Glu Glu Glu Glu Glu Glu
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(10)
<223> OTHER INFORMATION: This sequence may encompass 5-10 repeating
      'Arg' residues

<400> SEQUENCE: 10

Arg Arg Arg Arg Arg Arg Arg Arg Arg Arg
1               5                   10
```

```
<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Lys Lys Lys Lys Lys
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Glu Glu Glu Glu Glu
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Arg Arg Arg Arg Arg
1               5
```